United States Patent
Schnute et al.

(10) Patent No.: US 6,831,081 B2
(45) Date of Patent: Dec. 14, 2004

(54) 4-OXO-4,7-DIHYDROTHIENO[2,3-B] PYRIDINE-5-CARBOXAMIDES AS ANTIVIRAL AGENTS

(75) Inventors: Mark E. Schnute, Kalamazoo, MI (US); Fred L. Ciske, Lawton, MI (US); Michael J. Genin, Kalamazoo, MI (US); Joseph Walter Strohbach, Mendon, MI (US); Suvit Thaisrivongs, Kalamazoo, MI (US)

(73) Assignee: Pharmacia & Upjohn, Kalamazoo, MI (US)

( * ) Notice: Subject to any disclaimer, the term of this patent is extended or adjusted under 35 U.S.C. 154(b) by 0 days.

(21) Appl. No.: 10/649,298

(22) Filed: Aug. 27, 2003

(65) Prior Publication Data

US 2004/0110786 A1 Jun. 10, 2004

Related U.S. Application Data

(60) Provisional application No. 60/407,992, filed on Sep. 4, 2002.

(51) Int. Cl.$^7$ ............................................. A61K 31/435
(52) U.S. Cl. ................. 514/233.8; 514/232.2; 514/256; 514/269; 514/301; 546/114; 544/127; 544/298; 544/318
(58) Field of Search .......................... 546/114; 544/127, 544/298, 318; 514/232.2, 233.8, 256, 269, 301

(56) References Cited

U.S. PATENT DOCUMENTS 6,239,142 B1    5/2001    Schnute et al. ............. 514/301

FOREIGN PATENT DOCUMENTS

| EP | 443568 B1 | 2/1991 | ......... C07D/495/04 |
| JP | 08301849 | 11/1996 | ......... C07D/217/26 |
| WO | WO 95/28405 | 10/1995 | ......... C07D/495/04 |

*Primary Examiner*—Amelia A. Owens
(74) *Attorney, Agent, or Firm*—Karl Neidert; Bryan C. Zielinski; Peter Richardson

(57) ABSTRACT

The present invention provides a compound of formula as described herein, which are useful as antiviral agents, in particular, as agents against viruses of the herpes family.

55 Claims, No Drawings

4-OXO-4,7-DIHYDROTHIENO[2,3-B] PYRIDINE-5-CARBOXAMIDES AS ANTIVIRAL AGENTS

CROSS REFERENCE

Th is application claims the benefit of the following provisional application: U.S. Ser. No. 60/407,992, filed Sep. 4, 2002 under 35 USC a 19(e)(i), which is incorporated herein by reference in its entirety.

FIELD OF THE INVENTION

The present invention discloses 4-oxo-4,7-dihydrothieno [2,3-b]pyridine-5-carboxamides derivatives, and more specifically, provides compounds of formula (I) described herein below. These compounds are useful as antiviral agents, in particular, as age nts against viruses of the herpes family.

BACKGROUND OF THE INVENTION

The herpes viruses comprise a large family of double stranded DNA vies. They are also a source of the most common viral illnesses in man. Eight of the herpes viruses, herpes simplex virus types 1 and 2 (HSV-1 and HSV-2), varicella zoster virus (VZV), human cytomegalovirus (HCMV), epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. HCMV infection is also associated with cardiovascular disease and conditions including restenosis and atherosclerosis. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associate with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Infection by or reactivation of herpesviruses is associated with several cardiovascular diseases or conditions in the host such as atherosclerosis and restenosis resulting in inflation of coronary vessel walls. It is thought that in many patients suffering from restenosis following coronary atherectomy viral infection particularly by CMV plays an important role in the proliferation of the disease. Atherosclerosis is believed to be associated with the overall infectious disease burden in the host and particularly by the herpesviruses such as HSV, CMV, and EBV.

Infection in the animal population (livestock and companion) by strains of herpesviruses is endemic including cattle (Bovine herpesvirus 1-5, BHV), sheep (Ovine herpesvirus 1 and 2), dog (Canine herpesvirus 1), horse (Equine herpesvirus 1-8, EHV), cat (Feline herpesvirus 1, FHV), swine (pseudorabies virus, PRV), and many species of fowl. In the case of bovine herpesvirus infection, animals may suffer from ocular, respiratory, or digestive disorders. Pseudorabies is an extremely contagious viral pathogen infecting several species such as cattle, horses, dogs, cats, sheep, and goats leading to rapid death. The virus is benign in adult swine, however, it remains contagious and leads to high mortality in pigs under three weeks. Infection of horses by equine herpesvirus may lead to neurological syndromes, respiratory disease, and neonatal disease. Herpesvirus infection in cats leads to the disease known as feline viral rhinotracheitis (FVR) which is characterized by rhinitis, tracheitis, laryngitis, and conjunctivitis.

Compounds of the present invention demonstrate unexpected activity against the above reference herpesviral infections, particularly, human cytomegaloviral infection.

INFORMATION DISCLOSURE

U.S. Pat. No. 6,239,142 discloses compounds and their use to treat herpesvirus infections.

EP 443568 discloses compounds having angiotensin II antagonist activity and antihypertensive activity. WO95/28405 discloses compounds potentially useful for the treatment of sex-hormone dependent cancers and as contraceptives.

JP 08301849 discloses compounds useful as tachykinin receptor antagonists.

SUMMARY OF THE INVENTION

The present invention provides a compound of formula I:

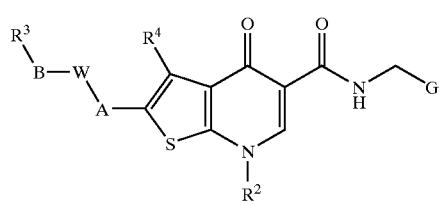

its enantiomeric, diastereomeric, or tautomeric isomer thereof, or a pharmaceutically acceptable salt thereof wherein, G is phenyl substituted with from one (1) to five (5) $R^1$ substituents;

each $R^1$ is independently
   (a) Cl,
   (b) Br,
   (c) F,
   (d) CN,
   (e) $C_{1-7}$alkyl, or
   (f) $NO_2$;

$R^1$ is
   (a) H,
   (b) $R^5$,
   (c) $NR^7R^8$,
   (d) $SO_2R^{10}$, or
   (e) $OR^9$;

A is $C_{1-7}$alkyl;

W is a five- (5) or six- (6) membered heterocyclic ring having one (1), two (2) or three (3) heteroatoms selected from the group consisting of O, S(O), and N wherein W is optionally substituted with one or more OH, oxo (=O), or $C_{1-7}$ alkyl;

B is
   (a) $C_{1-7}$alkyl optionally substituted by OH or $NR^7R^8$,
   (b) O, or
   (c) $NR^{11}$;

$R^3$ is
- (a) phenyl, optionally fused to a benzene or pyridine ring, and optionally substituted by $R^{12}$, wherein optionally any two adjacent $R^{12}$ substituents taken together constitute a group of the formula $-O(CH_2)O-$, $-(WC(=O)(CH_2)_jO-$, or $CH_2)_i-$, or
- (b) a five- (5) or six- (6) membered heteroaryl bonded via a carbon atom having one (1), two (2), or three (3) heteroatoms selected from the group consisting of O, S, and N—Z, wherein $R^3$ is optionally fused to a benzene or pyridine ring, and optionally substituted with one or more $R^{12}$, wherein Z is absence, H, or $C_{1-4}$alkyl;

$R^4$ is
- (a) H,
- (b) halo, or
- (c) $C_{1-4}$alkyl optionally substituted by halo;

$R^5$ is
- (a) $(CH_2)_mOCH_2CH_2OR^{11}$,
- (b) het, wherein said het is bound via a carbon atom,
- (c) aryl,
- (d) $C_{1-7}$alkyl which may be partially unsaturated and is optionally substituted by one or more $R^6$ substituents, or
- (e) $C_{3-8}$ cycloalkyl which may be partially unsaturated and optionally substituted by one or more $R^6$ or $C_{1-7}$alkyl optionally substituted by $R^6$;

$R^6$ is
- (a) $OR^9$,
- (b) $SR^9$,
- (c) $NR^7R^8$,
- (d) halo,
- (e) $CONR^7R^8$,
- (f) $CO_2R^9$,
- (g) het,
- (h) phenyl, optionally substituted by $R^{12}$,
- (i) CN,
- (j) oxo,
- (k) $SO_2NR^9R^{11}$,
- (l) $SO_m R^{10}$, or
- (m) $P(=O)(OR^{11})(R^{11}$;

$R^7$ and $R^8$ are independently
- (a) H,
- (b) aryl
- (c) $C_{1-7}$ alkyl which may be partially unsaturated and is optionally substituted by one or more $NR^{11}R^{11}$, $OR^{11}$, $SR^{11}$, $SO_mR^{10}$, $CONR^{11}R''$, $CO_2R^{11}$, het, aryl, cyano, or halo,
- (d) $C_{3-8}$cycloalkyl,
- (e) $(C=O)R^{10}$, or
- (f) $R^7$ and $R^8$ together with the nitrogen to which they are attached form a het;

$R^9$ is
- (a) H,
- (b) aryl,
- (c) het, wherein the het is bound through a carbon atom,
- (d) $C_{1-7}$alkyl which is optionally partially unsaturated and is optionally substituted by one or more aryl het, $OR^{11}$, $SR^{11}NR^{11}R^{11}$, halo, or $C_{3-8}$cycloalkyl substituents and which $C_{3-8}$cycloalkyl is optionally substituted by $OR^{11}$, or
- (e) $C_{3-8}$cycloalkyl which is optionally partially unsaturated and is optionally substituted by one or more halo, $OR^{11}$, $SR^{11}$, or $NR^{11}R^{11}$substituents;

$R^{10}$ is
- (a) aryl,
- (b) bet,
- (c) $C_{1-7}$alkyl which is optionally partially unsaturated and is optional substituted by one or more aryl, bet, $OR^{11}$, $SR^{11}$, $NR^{11}R^{11}$, halo, or $C_{3-8}$cycloalkyl substituents and which $C_{3-8}$ cycloalkyl is optionally substituted by $OR^{11}$, or
- (d) $C_{3-8}$ cycloalkyl which is optionally partially unsaturated and is optionally substituted by one or more halo, $OR^{11}$, $SR^{11}$, or $NR^{11}R^{11}$ substituents;

$R^{11}$ is
- (a) H, or
- (b) $C_{1-7}$alkyl;

$R^{12}$ is
- (a) halo,
- (b) $OR^{14}$,
- (c) $SR^{11}$,
- (d) $NR^7R^8$,
- (e) phenyl, optionally substituted by halo, $C_{1-7}$alkyl, or $C_{1-7}$alkoxy,
- (f) $C_{1-7}$alkyl which is optionally partially unsaturated and optionally substituted by $R^{13}$,
- (g) cyano,
- (h) nitro,
- (i) $CONR^7R^8$,
- (j) $SO_2NR^7R^8$,
- (k) $CO_2R^{11}$, or
- (l) $NHC(=O)R^{11}$;

$R^{13}$ is
- (a) phenyl, optionally substituted by halo, $C_{1-7}$alkyl, or $C_{1-7}$alkoxy,
- (b) $OR^{11}$,
- (c) $O(CH_2CH_2O)_nR^{11}$,
- (d) $NR^7R^8$, or
- (e) halo;

$R^{14}$ is
- (a) H
- (b) alkyl, optionally substituted by halo,
- (c) phenyl, optionally substituted by halo, $C_{1-7}$alkyl, or $C_{1-7}$alkoxy, or
- (d) $-(CH_2CH_2O)_nOR^{11}$;

i is 3 or 4;
j is 0 or 1;
k is 0, 1, or 2;
each n is independently 1, 2, 3, 4 or 5;
each m is independently 1 or 2;
wherein any aryl is optionally substituted with one or more substituents selected from the group consisting of halo, $OR^{11}$, $NR^{11}R^{11}$, cyano, $CO_2R^{11}$, or $C_{1-7}$alkyl in which said $C_{1-7}$allyl is optionally substituted by one to three halo, $OR^{11}$, or $NR^{11}R^{11}$; and
wherein any het is optionally substituted with one or more substituents selected from the group consisting of halo, $OR^{11}$, $NR^{11}R^{11}$, cyano, $CO_2R^{11}$, oxo (=O), or $C_{1-7}$alkyl in which said $C_{1-7}$alkyl is optionally substituted by one to three halo, $OR^{11}$, or $NR^{11}R^{11}$.

In another aspect, the present invention also provides:

A pharmaceutical composition which comprises a pharmaceutically acceptable carrier and an effective amount of a compound of formula I, a method of treating and preventing herpesviral infections in a mammal comprising administering to a mammal in need thereof a compound of formula I, or a pharmaceutically acceptable salt thereof, a method for inhibiting a viral DNA polymerase comprising contacting, in vivo or in vitro, the polymerase with an effective inhibitory amount of a compound of formula I, or a pharmaceutically acceptable salt thereof, a compound of formula I or a pharmaceutically acceptable salt thereof for use in medical treatment or prevention of a herpesviral infection in a mammal.

The invention also provides novel intermediates and processes disclosed herein that are useful for preparing compounds of formula I.

DETAILED DESCRIPTION OF THE INVENTION

For the purpose of the present invention, the carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $(C_{1-7})$ alkyl refers to alkyl of one to seven carbon atoms, inclusive, or methyl, ethyl, propyl, butyl, pentyl, hexyl, and heptyl, straight and branched forms thereof.

The term "halo" or "halogen" refers to the elements fluorine (F), chlorine (Cl), bromine (Br) and iodine (I).

The term "$C_{3-8}$cycloalkyl" refers to a non-aromatic carbocyclic ring having from 3 to 8 carbon atoms.

The term "alkoxy" refers to the group RO—, wherein R is alkyl or cycloalkyl as defined above.

The term "aryl" refers to a phenyl radical or an ortho-fused bicyclic carbocyclic radical wherein at least one ring is aromatic.

The term "het" refers to a four- (4), five- (5), six- (6), or seven- (7) membered saturated or unsaturated heterocyclic ring having one (1), two (2), or three (3) heteroatoms selected from the group consisting of oxygen (—O—), sulfur (—S—), oxygenated sulfur such as sulfinyl (S═O) and sulfonyl (S(═O)₂), or nitrogen, which said heterocyclic ring is optionally fused to a benzene ring or is an N-oxide thereof.

The term "heteroaryl" refers to aromatic heterocyclic groups.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

In particular, it is understood that compounds of formula I wherein $R^2$ is hydrogen can exist in the corresponding tautomeric "enol" form, such as formula II, and that such tautomers are included as compounds of the invention.

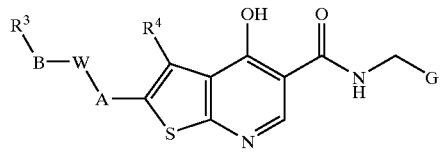

The compounds of the present invention are generally named according to the IUPAC or CAS nomenclature system "Pharmaceutically acceptable salts" refers to those salts which possess the biological effectiveness and properties of the parent compound and which are not biologically or otherwise undesirable.

"Mammal" refers to human and animals. Animals specifically refer to, for example, food animals or companion animas.

"Optionally" or "ray be" means that the subsequently described event or circumstance may, but need not, occur, and that the description includes instances where the event or circumstance occurs and instances in which it does not.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

Specifically, G is 4-chlorophenyl, 4-fluorophenyl, 3,4-dichlorophenyl, 3,4-difluorophenyl 2,4-chlorophenyl, 2,4-difluorophenyl, 4-chloro-2-fluorophenyl, 2-chloro-4-fluorophenyl, 3,4,5-trifluorophenyl, 4-bromophenyl, 4-methylphenyl, 4-cyanophenyl, or 4-nitrophenyl.

Specifically, G is phenyl substituted at the 4-position by $R^1$.

Specifically, $R^1$ is Cl, F, or cyano.

Specifically, $R^1$ is Cl.

Specifically, $R^1$ is P.

Specifically, G is 4-chlorophenyl.

Specifically, G is 4-fluorophenyl.

Specifically, $R^2$ is H.

Specifically, $R^2$ is $R^5$.

Specifically, $R^2$ is $C_{1-7}$alkyl which is optionally substituted with one or more $R^6$ substituents.

Specifically, $R^2$ is methyl.

Specifically, $R^2$ is ethyl.

Specifically, $R^2$ is $C_{1-3}$alkyl substituted with one or two hydroxy.

Specifically, $R^2$ is 2-hydroxyethyl, 3-hydroxypropyl, or 2,3-dihydroxypropyl.

Specifically, $R^2$ is $C_{1-4}$alkyl substituted by $C_{1-4}$alkoxy.

Specifically, $R^2$ is $C_{1-4}$alkyl substituted by methoxy.

Specifically, $R^1$ is 2-methoxyethyl.

Specifically, $R^2$ is $C_{1-4}$alkyl substituted by $NR^7R^8$.

Specifically, A is $Cl_{1-4}$alkyl

Specifically, A is methyl.

Specifically, W is a six- (6) membered heterocyclic ring having one (1), two (2), or three (3) heteroatoms selected from the group consisting of oxygen, sulfur, or nitrogen, wherein W is optionally substituted with $C_{1-4}$ alkyl Specifically, W is morpholine, piperidine, or piperazine.

Specifically, W is five- (5) membered heterocyclic ring having one (1), two (2), or three (3) heteroatoms selected from the group consisting of oxygen, sulfur, or nitrogen, wherein W is optionally substituted with $C_{1-4}$ allyl.

Specifically, W is pyrrolidine.

Specifically, B is $C_{1-4}$alkyl.

Specifically, B is methyl.

Specifically, B is methyl substituted with a hydroxy.

Specifically, $R^3$ is phenyl

Specifically, $R^1$ is phenyl substituted with one or more $R^{12}$.

Specifically, $R^3$ is 2-cyanophenyl 3-cyanophenyl, 4-cyanophenyl, 2-bromophenyl 3-bromophenyl, 4-bromophenyl, 2-chlorophenyl, 3-chlorophenyl, 4-chlorophenyl, 2-hydroxyphenyl, 3-hydroxyphenyl, 4-hydroxyphenyl, 2-methoxyphenyl, 3-methoxyphenyl, 4-methoxyphenyl, 2-methylphenyl, 3-methylphenyl, 4-methylphenyl, 2-ethylphenyl, 3-ethylphenyl 4-ethylphenyl, 2-trifluoromethylphenyl, 3-trifluoromethylphenyl 4-trifluoromethylphenyl, 2-nitrophenyl, 3-nitrophenyl, 4-nitrophenyl, 4-phenoxyphenyl, 3-phenoxyphenyl, 3-(4-chlorophenoxy)phenyl, 3-(4-methoxyphenoxy)phenyl 3-(4-methylphenoxy)phenyl, 3,4dibromophenyl, 2-chloro-5-trifluoromethylphenyl 3,5-dibromophenyl, 3,5dibromo-6-methoxyphenyl, 3,5-di(trifluoromethyl)phenyl, 3-cyano-4-fluorophenyl, 3-bromo-4fluorophenyl 2-bromophenyl 3-bromo-6-fluorophenyl, 4-bromo-6-fluorophenyl, 3-bromo-6-hydroxyphenyl, 3-bromo-4-methoxyphenyl, 4-(1H-imidazol-1-yl)phenyl, 3, bromo-6-methoxyphenyl, 4-nitrophenyl, 4-chloro-5-fluorophenyl, 2-chloro-6-fluorophenyl, 2-chloro-4-fluorophenyl, 2-fluoro-4-methoxyphenyl, 4-hydroxy-5-methoxyphenyl, 4-(acetylamino)phenyl, 3-(acetylamino)phenyl, 4-hydroxy-5-methylphenyl, 2-thiomethylphenyl, 3-fluoro-2-methylphenyl, 2-trifluoromethoxyphenyl, 3-trifluoromethoxyphenyl, 4trifluoromethoxyphenyl, 4-hydroxymethylphenyl, 3-hydroxymethylphenyl, 2-hydroxymethylphenyl, 4-aminophenyl, 3-aminophenyl, 2-fluoro-4-trifluoromethylphenyl, 2-methyl-4-methoxyphenyl 4-dimethylaminophenyl, 2,3-dimethylphenyl, 2,4-dimethylphenyl, 3,4-dimethylphenyl 3,5-dimethylphenyl, 4-hydroxy-5-methoxyphenyl, 4-(2-hydroxyethoxy)phenyl, 4-morpholin-4-ylphenyl, 1,1'-biphenyl-4-yl, 1,1'-biphenyl-3-yl, 2-fluorophenyl 3-fluorophenyl, 4fluorophenyl, 2,3-difluorophenyl, 3,4-difluorophenyl, 2,6-difluorophenyl, 2,5-difluorophenyl 2,4-difluorophenyl, 3,5-difluorophenyl 2,3,4-trifluorophenyl, 3,4,5-trifluorophenyl, 2,4,6-trifluorophenyl, 2,3,6-trifluorophenyl, 2,3,5-trifluorophenyl, or 2,3,4,5,6-pentafluoro-phenyl.

Specifically, $R^3$ is 2-oxo-2,3-dihydro-1,3-benzoxazol-5-yl, 3-oxo-3,4-dihydro-2H-1,4-benzoxazin-6-yl, 2,3-dihydro-1,4-benzodioxan-6-yl, 1,3-benzodioxol-5-yl, 1,3-benzodioxol-4-yl, 6-chloro-1,3-benzodioxol-5-yl, or 7-methoxy- 1,3-benzodioxol-5-yl.

Specifically, $R^3$ is naphthyl, optionally substituted with one or more $R^{12}$.

Specifically, $R^3$ is 1-naphthyl or 2-naphthyl.

Specifically, $R^3$ is 2-methoxy-1-naphthyl, 4-methoxy-1-naphthyl, 4-dimethyl-amino-1-naphthyl, 4-methyl-1-naphthyl, 4-hydroxy-1-naphthyl, or 6-methoxy-2-naphthyl.

Specifically, $R^3$ is phenyl fused to a pyridine ring, optionally substituted with one or more $R^{12}$.

Specifically, $R^3$ is quinolin-8-yl, isoquinolin-8-yl, isoquinolin-5-yl, quinolin-5-yl, quinolin-7-yl, isoquinolin-7-yl, isoquinolin-6-yl, or quinolin-6-yl.

Specifically, $R^3$ is a five- (5) membered heteroaryl bonded via a carbon atom having one (1) or two (2) heteroatoms selected from the group consisting of O, S, and N—Z.

Specifically Z is absence.

Specifically Z is H.

Specifically Z is methyl, ethyl, propyl, butyl, 2-methylpropyl.

Specifically, $R^3$ is 2-furyl 3-furyl, thien-2-yl, thien-3-yl, 1H-pyrrol-2-yl, 1H-pyrrol-3-yl, 1H-imidazol-4-yL 1H-imidazol-2-yl, 1,3-thiazol-2-yl, 1,3-thiazol-5-yl, 1H-pyrazol-5-yl, 1-methyl-1H-pyrrol-2-yl, 1-ethyl-1H-pyrrol-2-yl, 1-propyl-1H-pyrrol-2-yl, 1-methyl-1H-imidazol-yl, 1-methyl-1H-imidazol-2-yl, 1-ethyl-1H-imidazol-4-yl, or 1-ethyl-1H-imidazol-2-yl.

Specifically, $R^3$ is a f (5) membered heteroaryl bonded via a carbon atom having one (1) or two (2) heteroatoms selected from the group consisting of O, S, and N—Z, wherein $R^3$ is substituted by $R^{12}$.

Specifically, $R^3$ is 5-methyl-2-furyl, 5-trifluoromethyl-2-furyl, 2,5-dimethyl-3-furyl, 4,5-dimethyl-2-furyl, 4-methyl-2-furyl, 5-hydroxymethyl-2-furyl, 5-((dimethylamino)methyl)-2-furyl 5-ethyl-2-furyl, S-bromo-2-furyl 4,5-dibromo-2-furyl, 5-chloro-2-furyl, 5-phenyl-2-furyl 4-phenyl-2-furyl, 5-(2-chlorophenyl)-2-furyl, 5-(3-chlorophenyl)-2-furyl, 5-(4-chlorophenyl)-2-furyl, 5-(2,4-dichlorophenyl)-2-furyl, 5-(2,5-dichlorophenyl)-2-furyl, 5-(2,4,6-trichlorophenyl)-2-furyl, 5-cyanothien-2-yl, 4-bromothien-2-yl, or 5chlorothien-2-yl.

Specifically, $R^3$ is a five- (5) membered heteroaryl bonded via a carbon atom having one (1) or two (2) heteroatoms selected from the group consisting of O, S, and N—Z, wherein $R^3$ is fused to a benzene or pyridine ring.

Specifically, $R^3$ is benzofuran-2-yl, benzofuran-3-yl, benzothien-2-yl, benzothien-3-yl, 1,3-benzoxazol-2-yl, 1,3-benzothiazol-2-yl, 1H-indol-3-yl 1H-indol-2-yl, 1,3-benzothiazol-2-yl, furo[2,3-b]pyridin-2-yl, furo[2,3-c]pyridin-2-yl, furo[3,2-c]pyridin-2-yl, furo[3,2-b]pyridin-2-yl, furo[2,3-b]pyridin-3-yl, furo[2,3-c]pyridin-3-yl, furo[3,2-c]pyridin-3-yl, furo[3,2-b]pyridin-3-yl, 1-methyl-1H-indol-2-yl, 1-ethyl-1H-indol-2-yl.

Specifically, $R^3$ is a five- (5) membered heteroaryl bonded via a carbon atom having one (1) or two (2) heteroatoms selected from the group consisting of O, S, and N—Z, wherein $R^3$ is fused to a benzene or pyridine ring, and is substituted with one or more $R^{11}$.

Specifically, $R^3$ is 3-chloro-1-benzofuran-2-yl, 2-phenyl-1H-indol-3-yl, 2-(4-fluorophenyl)-1H-indol-3-yl, 5-fluoro-1H-indol-3-yl, 2-methyl-1H-indol-3-yl, 5-methyl-1H-indol-3-yl, 6-methyl-1H-indol-3-yl, 7-methyl-1H-indol-3-yl, 3-methyl-1-benzothien-2-yl, 3-phenyl-1H-pyrazol-4-yl, or 1,3dimethyl-1H-pyrazol-4-yl.

Specifically, $R^3$ is 1-methyl-1H-1,2,4-triazol-5-yl.

Specifically, $R^3$ is a six- (6) membered heteroaryl bonded via a carbon atom having one (1), two (2), or three (3) nitrogen atoms.

Specifically, $R^3$ is pyridin-2-yl, pyridin-3-yl, pyridin-4yl, pyrazin-2-yl, pyrimidin-2-yl, pyrimidin-4-yl, 2-pyridazin-3-yl, pyrimidin-5-yl, pyridazin-4-yl, (1,2,4-triazin-6-yl, (1,2,4-triazin-3-yl), (1,3,5-triazin-2-yl), or (1,2,4-triazin-5-yl).

Specifically, $R^3$ is a six- (6) membered heteroaryl bonded via a carbon atom having one (1) or two (2) nitrogen atoms.

Specifically, $R^3$ is pyridin-2-yl, pyridin-3-yl, pyridin-4-yl, pyrazin-2-yl, pyrimidin-2-yl, pyrimidin-4-yl, 2-pyridazin-3-yl, pyrimidin-5-yl, or pyridazin-4-yl.

Specifically, $R^3$ is a six- (6) membered heteroaryl bonded via a carbon atom having one (1), two (2), or three (3) nitrogen atoms wherein $R^3$ is fused to a benzene ring.

Specifically, $R^3$ is isoquinolin-3-yl, quinolin-3-yl, quinolin-2-yl, quinazolin-2-yl, quinoxalin-2-yl, cinnolin-3-yl, (1,2,4-benzotriazin-3-yl), isoquinolin-1-yl, isoquinolin-4-yl, quinolin-4-yl, quinazolin-4-yl, phthalazin-1-yl, or cinnolin-4-yl.

Specifically, $R^3$ is a six- (6) membered heteroaryl bonded via a carbon atom having one (1) or two (2) nitrogen atoms wherein $R^3$ is fused to a benzene ring.

Specifically, $R^3$ is isoquinolin-3-yl, quinolin-3-yl, quinolin-2-yl, quinazolin-2-yl, quinoxalin-2-yl, cinnolin-3-yl, isoquinolin-1-yl, isoquinolin-4-yl, quinolin-4-yl, quinazolin-4-yl, phthalazin-1-yl, or cinnolin-4-yl.

Specifically, $R^3$ is a six- (6) membered heteroaryl bonded via a carbon atom having one (1) nitrogen atom wherein $R^3$ is fused to a benzene ring.

Specifically, $R^3$ is isoquinolin-3-yl, quinolin-3-yl, quinolin-2-yl, isoquinolin-1-yl, isoquinolin-4-yl, quinolin-4-yl.

Specifically, $R^4$ is hydrogen.

Specifically, $R^1$ is methyl.

Examples of the present invention include, but are not limited to the following:

(1) 2-(((3S-3-Benzylmorpholin-4-yl)methyl)-N-(4-chlorobenzyl-7-methyl-4-oxo-4,7dihydrothieno[2,3-b]pyridine-5-carboxamide, (2) N-(4-Chlorobenzyl)-2-(((2R*)-2-((S*)-hydroxy(phenyl)methyl)pyrrolidin-1-yl)-methyl)-7-methyl-4-oxo-4,7-dihydrothieno[2,3-b]pyridine-5carboxamide, (3) N-(4 Chlorobenzyl)-2-(((2R*)-2-((R*)-hydroxy(pyridin-2-yl)methyl)pyrrolidin-t-yl)methyl)-7-methyl-4-oxo-4,7-dihydrothieno[2,3-b]pyridine-5-carboxamide, (4) N-(4-Chlorobenzyl)-2-(((2R*)-2-((R*)-2-furyl(hydroxy)methyl)pyrrolidin-1-yl)methyl)-7-methyl-4-oxo-4,7-dihydrothieno[2,3-b]pyridine-5-carboxamide, (5) N-(4-chlorobenzyl)-2-(((2R)-2-((R)-hydroxy(1,3-thiazol-2-yl)methyl)-pyrrolidin-1-yl}methyl)-7-methyl-4-oxo-4,7-dihydrothieno[2,3-b]pyridine-5-carboxamide, (6) N-(4-chlorobenzyl)-2-(((2R)-2-((R)-hydroxy(thien-2-ylmethyl)pyrrolidin-1-yl}methyl)-7-methyl-4-oxo-4,7-dihydrothieno[2,3-b]pyridine-5-carboxamide, (7) 2-(((2R)-2-((R)-1,3-benzothiazol-2-yl(hydroxy)methyl)pyrrolidin-1-yl)methyl)-N-(4-chlorobenzyl)-7-methyl-oxo-4,7-dihydrothieno[2,3-b]pyridine-5-carboxamide, (8) N-(4-chlorobenzyl-2-(((2R)-2-((R)-hydroxy(1,3-thiazol-5-yl)methyl)-pyrrolidin-1-yl)methyl)-7-methyl-4-oxo-4,7-dihydrothieno[2,3-b]pyridine-5-carboxamide, (9) N-(4-chlorobenzyl)-2-(((2R)-2-((R)-hydroxy(pyridin-2-yl)methyl)pyrrolidin-1-yl)methyl)-7-methyl-4-oxo-4,7-dihydrothieno[2,3-b]pyridine-5-carboxamide,

(10) N-(4chlorobenzyl)-2((2R)-2-((S)-hydroxy(pyridin-3-yl)methyl)pyrrolidin-1-yl)methyl)-7-methyl-4-oxo-4,7-dihydrothieno[2,3-b]pyridine-5-carboxamide,

(11) N-(4-chlorobenzyl)-24((2R)-2-((S)-hydroxy(pyrimidin-5-yl)methyl)pyrrolidin-1-yl)methyl)-7-methyl-4-oxo-4,7-dihydrothieno[2,3-b]pyridine-5-carboxamide,

(12) N-(4chlorobenzyl)-2-(((2R)-2-((R)-hydroxy(1H-imidazol-2-yl)methyl)-pyrrolidin-1-yl)methyl)-7-methyl-4-oxo-4,7-dihydrothieno[2,3-b]pyridine-5-carboxamide,

(13) 2-(((2R)-2-((R)-1,3-benzoxazol-2-yl(hydroxy)methyl)pyrrolidin-1-yl)methyl)-N-(4-chlorobenzyl)-7-methyl-4-oxo-4,7-dihydrothieno[2,3-b]pyridine-5-carboxamide,

(14) N-(4-chlorobenzyl)-2-(((3R)-3-((R)-hydroxy(phenyl)methyl)morpholin-4-yl)-methyl)-7-methyl-4-oxo-4,7-dihydrothieno[2,3-b]pyridine-5-carboxamide,

(15) N-(4-chlorobenzyl)-2-(((3R)-3-((S)-hydroxy(phenyl)methyl)morpholin 4-yl-methyl)-7-methyl-4-oxo-4,7-dihydrothieno[2,3-b]pyridine-5-carboxamide,

(16) N-(4-chlorobenzyl)-7-ethyl-2-(((2R*)-2-((S*)-hydroxy(phenyl)methyl)-pyrrolidin-1-yl)methyl)-4-oxo-4,7-dihydrothieno[2,3-b]pyridine-5-carboxamide,

(17) N-(4-chlorobenzyl)-7-ethyl-24((3R)-3-((S)-hydroxy(phenyl)methyl)morpholin-4-yl)methyl)-4-oxo-4,7-dihydrothieno[2,3-b]pyridine-5-carboxamide,

(18) N-(4-chlorobenzyl)-2-(((2R*)-2-((S*)-hydroxy(phenyl)methyl)pyrrolidin-1-yl)methyl)-4-oxo-7-propyl-4,7-dihydrothieno[2,3-b]pyridine-5-carboxamide,

(19) N-(4-chlorobenzyl)-2-(((3R)-3(S)-hydroxy(phenyl)methyl)morpholin-4-yl)-methyl)-4-oxo-7-propyl-4,7-dihydrothieno[2,3-b]pyridine-5-carboxamide,

(20) N-(4 chlorobenzyl)-2-(((2R*)-2-((S*)-hydroxy(phenyl)methyl)pyrrolidin-1-yl)methyl)-7-(2-methoxyethyl)-4-oxo-4,7-dihydrothieno[2,3-b]pyridine-5-carboxamide,

(21) N-(4 chlorobenzyl)-2-(((3R)-3-((S)-hydroxy(phenyl)methyl)morpholin-4-yl)-methyl)-7-(2-methoxyethyl)-4-oxo-4,7-dihydrothieno[2,3-b]pyridine-5-carboxamide,

(22) N-(4-chlorobenzyl)-2-(((2R*)-24(S*)-hydroxy(phenyl)methyl)pyrrolidin-1-yl)methyl)-7-(2-morpholin-4-ylethyl)-4-oxo-4,7-dihydrothieno[2,3-b]pyridine-5-carboxamide,

(23) N-(4-chlorobenzyl)-2-(((3R)-3-((S)-hydroxy(phenyl)methyl)morpholin-4-yl)-methyl)-7-(2-morpholin-4-ylethyl)-4-oxo-4,7-dibydrothieno[2,3-b]pyridine-5-carboxamide,

(24) N-(4-chlorobenzyl)-2-(((2R*)-2-((S*)-hydroxy(phenyl]methyl)pyrrolidin-1-yl)-methyl)-3,7-dimethyl-4-oxo-4,7-dihydrothieno[2,3-b]pyridine-5-carboxamide,

(25) N-(4-chlorobenzyl)-2-(((3R)-3-((S)-hydroxy(phenyl)methyl)morpholin-4-yl-methyl)-3,7-dimethyl-oxo-4,7-diydrothieno[2,3-b]pyridine-5-carboxamide, or pharmaceutically acceptable salts thereof.

Charts A-I describe the preparation of the compounds of formula (I) of the present invention. All of the starting materials are prepared by procedures described in these charts, by procedures well known to one of ordinary skill in organic chemistry or can be obtained commercially. All of the final compounds of the present invention are prepared by procedures described in these charts or by procedures analogous thereto, which would be well known to one of ordinary skill in organic chemistry.

Compounds in which the heterocycle W attaches to the alkyl group A through a nitrogen atom are prepared as described in Chart A. Compounds of the form A. 1 in which X is a leaving group (e.g. mesylate, chloride, or bromide) are treated with a heterocyclic secondary amine of the formula H—W—B—$R^3$ (wherein W, B and $R^3$ are as defined above and in the claims) in the presence of a non-nucleophilic base (e.g. diisopropylethylamine) in a polar solvent (e.g. DMF) to afford products of the formula A.2. It would be understood by those skilled in the art that in some cases transient protection of hydroxyl and other Lewis basic or acidic functionality present in H—W—B—$R^3$ may be required to facilitate the coupling described in Chart A for which procedures are well established (Greene, T. W.; Wuts, P. G. M. *Protective Groups in Organic Synthesis,* 1999).

CHART A

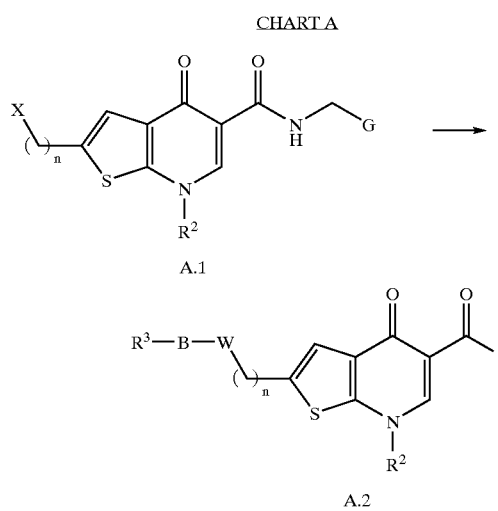

The precursors A.1 are available from the corresponding alcohols (X=OH) by treatment with methanesulfonyl chloride in the presence of an organic base (e.g. pyridine or 2,4,6-collidine) and if needed an activating agent (e.g. DMAP), Chart B. Alternatively where n is 1, compounds of the formula A are available by treatment of a tertiary amino derivative (e.g. X=N(CH$_3$)$_2$ or 4-morpholinyl) with ethyl chloroformate in an appropriate solvent (e.g. chloroform, dichloromethane, 1,2-dichloroethane, or benzene).

CHART B

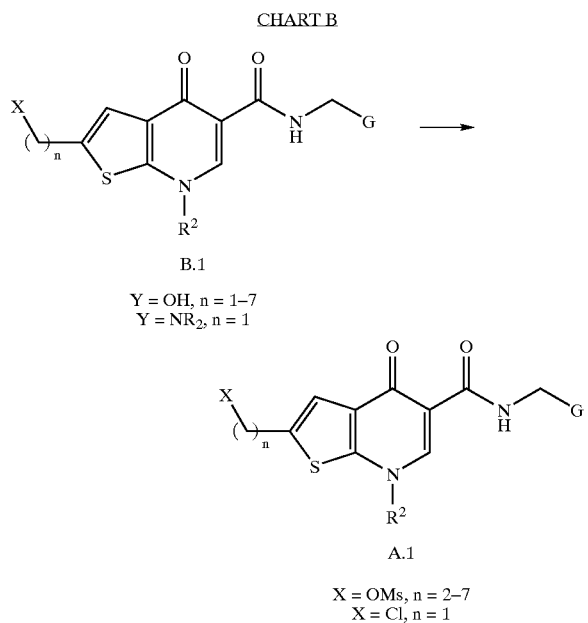

Subsequently, compounds of the general formula B.1 are prepared according to procedures described in U.S. Pat. No. 6,239,142 or exemplified in Charts C–E below.

As described in Chart C, 3-bromo-2-chlorothiophene (C.1) is metalated with lithium diisopropyl amide in tetrahydrofuran at low temperature followed by addition to paraformaldehyde to provide alcohol C.2. The free hydroxyl is protected employing common methodology (Greene, T. W.; Wuts, P. G. M. *Protective Groups in Organic Synthesis*, 1999) such as the tert-butyldimethylsilyl ether (TBS) by treatment with the corresponding silyl chloride and a weak base (e.g. imidazole) in a polar solvent (e.g. DMF). Metalation of C.3 with n-butyl lithium followed by addition to N-methoxy-N-methylacetamide provides the methyl ketone C.4. Condensation of C.4 with diethyl carbonate in the presence of a strong base (e.g. sodium hydride) affords ketoester C.5. Compound C.5 is then refluxed in a mixture of acetic anhydride and triethylorthoformate to afford an intermediate enol ether which is then condensed with a primary amine or aniline (e.g. R$^2$NH$_2$) to provide a compound of the formula C.6. The resulting enamines are cyclized by heating in the presence of a base (e.g. sodium hydride, potassium carbonate, or potassium tert-butoxide) in an appropriate solvent (e.g. THF, DMF, or tert-butanol) to provide C.7. Esters of the formula C.7 are converted to amides of the general formula C.8 by either (a) treatment with a substituted benzylamine (e.g. 4-chlorobenzylamine, 4-fluorobenzylamine, or 4-bromobenzylamine) at high temperature or (b) saponification by treatment with an inorganic base such as sodium hydroxide to afford the corresponding carboxylic acid

CHART C

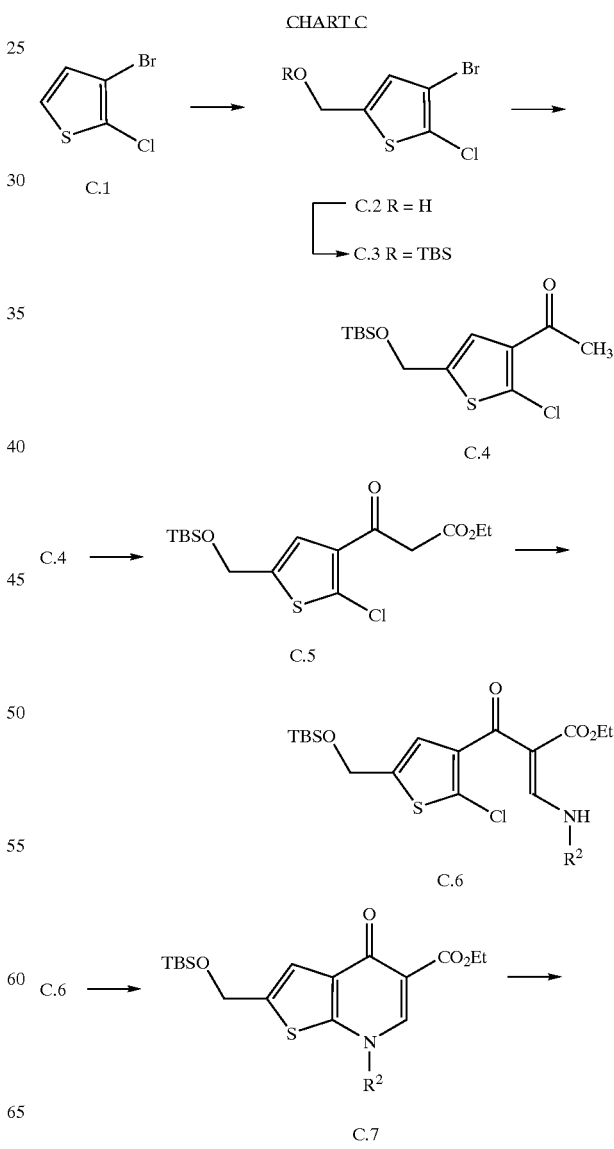

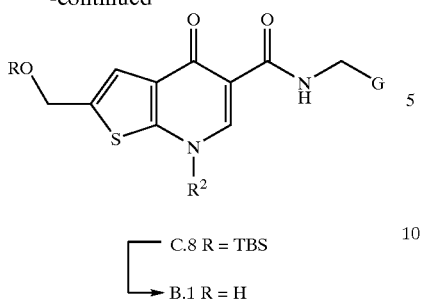

C.8 R = TBS
B.1 R = H which is then coupled with a substituted benzylamine mediated by 1,1'-carbonyl-diimidazole (or other suitable carboxylic acid activating agent). Subsequent deprotection of the hydroxyl protecting group to afford B.1 is accomplished through common procedures such as treatment with tetrabutylammonium fluoride in the case of silyl ether protection.

Compounds of formula B.1 (Y=NR$_2$, n=1) may be prepared as described in Chart D. 3-Bromo-2-chlorothiophene (C.1) is metalated with lithium diisopropyl amide in tetrahydrofuran at low temperature and condensed with N,N-dimethylformamide to afford the carboxaldehyde D.1. Reductive amination of D.1 by treating with an amine (e.g. morpholine), acetic acid, and an appropriate reducing agent (e.g. sodium triacetoxyborohydride) affords thiophenes of the formula D.2. Metalation of D.2 with n-butyl lithium followed by addition to N-methoxy-N-methylacetamide provides the methyl ketone D.3. Condensation of D.3 with diethyl carbonate in the presence of a strong base (e.g. sodium hydride) affords ketoester D.4. The resulting ketoester is then treated with a benzylamine (e.g. 4-chlorobenzylamine, 4-fluorobenzylamine, or 4bromobenzylamine) in refluxing xylene to provide

CHART D

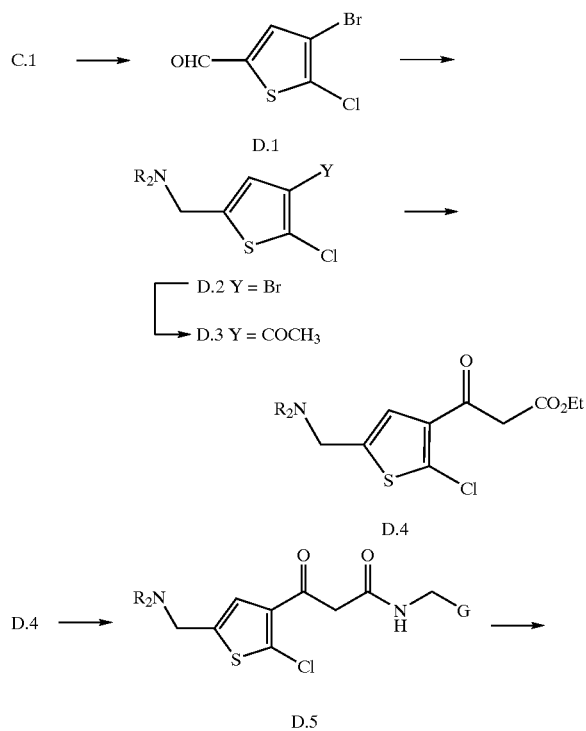

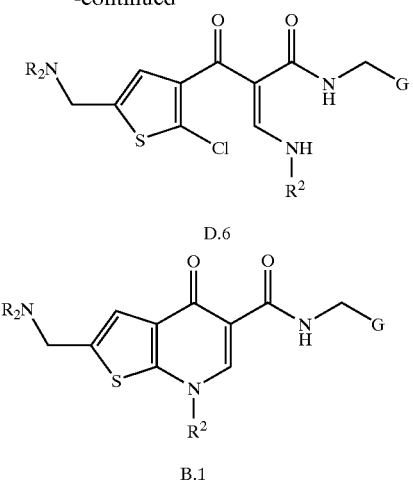

D.6

B.1 ketoamides of the formula D.5. Compound D.5 is then refluxed in a mixture of acetic anhydride and triethylorthoformate to afford an intermediate enol ether which is then condensed with a primary amine or amine (e.g. R$^2$NH$_2$) to provide a compound of the formula D.6. The resulting enamines are cyclized by heating in the presence of a base (e.g. sodium hydride, potassium carbonate, or potassium tert-butoxide) in an appropriate solvent (e.g. THF, DMF, or tert-butanol).

Alternatively, compounds of formula B.1 (Y=OH) may be prepared as described in Chart B. Ethyl 4-hydroxythieno[2,3-b]pyridine-S-carboxylate (*J. Heterocyclic Chem.* 1977, 14, 807) is metallated with from two to six equivalents of lithium diisopropylamide at low temperature and is then reacted with dimethylformamide to provide compound B.2. Treatment of B.2 with an appropriate reducing agent (e.g. NaBH$_4$) in a polar solvent (e.g. ethanol) affords the alcohol B.3. The resulting ester is then reacted with a substituted benzylamine (e.g. 4-chlorobenzylamine, 4-fluorobenzylamine, or 4-bromobenzylamine) at high temperature or under other common amide forming conditions well known to those skilled in the art to provide compounds of the formula E.4. Compound B.4 is alkylated at the ring nitrogen by treatment with an optionally substituted alkyl halide or alkyl sulfonate ester in the presence of a base (e.g. potassium carbonate) or by reaction with an optionally substituted alkanol under Mitsunobu conditions to afford compounds of the general formula B.1. Specific examples of such alkyl halides used in this reaction include but are not limited to iodomethane, iodoethane, 1-iodopropane, 1-iodobutane, and 1-bromo-2-methoxyethane. It would be understood by those skilled in the art that in some cases transient protection of hydroxyl functionality present in the R$^2$X (X=halo or sulfonate) or R$^2$OH reagent used in the above step may be required to facilitate the coupling described in Chart B or subsequent chemistry described in Charts A–B. Specific examples of such protected-hydroxyalkyl halides used in this reaction include but are not limited to 2-(2-bromoethoxy)tetrahydro-2H-pyran, 2-(3-bromopropoxy)tetrahydro-2H-pyran, 4bromomethyl)-2,2-dimethyl-1,3-dioxolane, 2-(2-(2-chloroethoxy)ethoxy)tetrahydro-2H-pyran, and 2-(chloromethoxy)ethyl benzoate. Procedures to deprotect these cases at the final or intermediate stage are well established (Greene, T. W.; Wuts, P. G. M. *Protective Groups in Organic Synthesis*, 1999).

CHART E

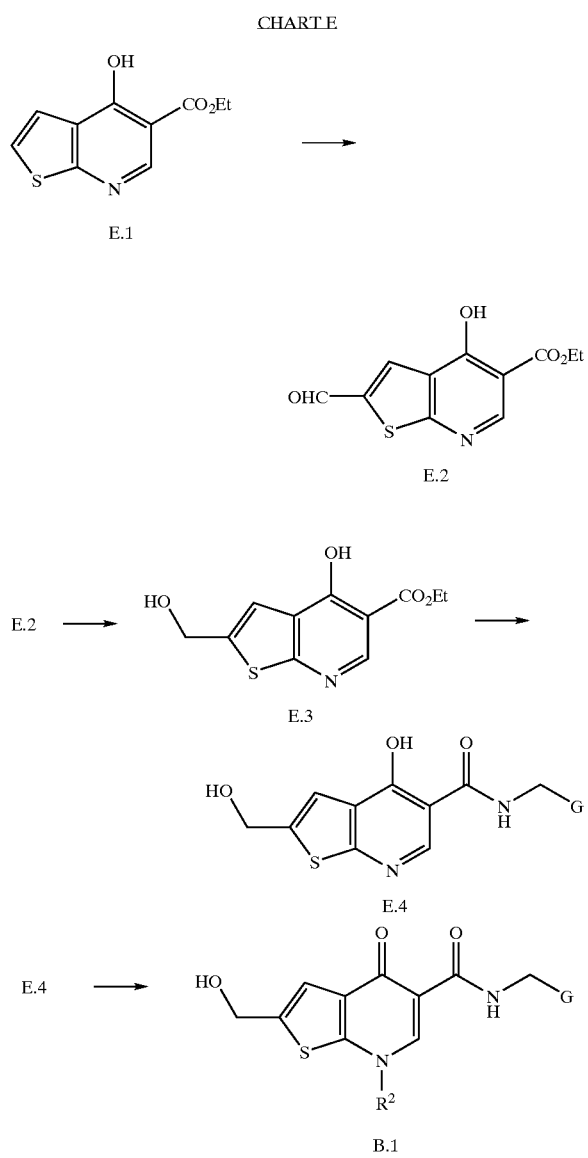

Specific secondary amines described in Chart A of the formula H—W—B—R³ are prepared according to literature procedures or adaptations there of, Chart F. Amines of the formula F.1 may be prepared by procedures described by Cooper, G. F.; McCarthy, K E.; Martin, M. G. *Tetrahedron Lett.* 1992, 33, 5895–5896 (a specific example of R³ being 3,4-dimethoxyphenyl); Gaur, S. P.; Jain, P. C.; Anand, N. *Ind. J. Chem. B,* 1982, 21, 46–51 (specific examples of R³ being phenyl, 3-methoxyphenyl, 1-naphthyl, and 2-naphthyl. Amines of the formula F.2 may be prepared by procedures described by Tsutsunu, S.; Okonogi, T; Shlbahara, S.; Ohuchi, S.; Hatsusluba, B.; Patchett, A A; Christensen, B. G. *J. Med. Chem.* 1994, 37, 3492–3502 (specific examples of R³ being thiazol-2-yl, thiopen-2-yl, benzthiazol-2-yl, thiazol-5-yl, imidazol-2-yl, pyridin-2-yl, pyrimidin-3-yl, pyrimidin-5-yl, benzoxazol-2-yl, oxazolo[4,5-b]pyridin-2-yl, thiazolin-2-yl, and thiazol-4-yl); Sanner, M. A. *Tetrahedron Lett.* 1989, 30, 1909–1912 (specific examples of R³ being 4-fluorophenyl, 4-chlorophenyl, 4-bromophenyl, 4-methylphenyl, and 4-methoxyphenyl). Amines of formula F.3 may be prepared by procedures described by Gottlieb, L.; Meyers, A. I. *Tetrahedron Lett.* 1990, 31, 47234726 (a specific example of R³ being phenyl); Kanao, M.; Hashizume, T.; Ichikawa, Y.; Irie, K; Satoh, Y.; Isoda, S. *Chem. Pharm. Bull.* 1982, 30, 180–188 (a specific example of R³ being 4methoxyphenyl); Cardellini, M.; Claudi, F.; Perlini, V.; Balduini, W.; Cattabeni, F.; Cimino, M. *Farmaco Ed. Sci.* 1987, 42, 307–318 (specific examples of R³ being 3-methoxyphenyl and 3,4-dimethoxyphenyl); Panizzon, L. *Helv. Chim. Acta* 1944, 27, 1748–1456 (a specific example of R³ being naphth-1-yl); Seibert, R A.; Norton, T. P; Bensen, A. A; Bergstrom, F. W. *J. Am. Chem. Soc.* 1946, 68, 2721–2723 (a specific example of R³ being quinolin-2-yl). Amines of formula F.4 may be prepared by procedures described by Sanner, M. A. *Tetrahedron Lets.* 1989, 30, 1909–1912 (specific examples of R³ being phenyl, 4-fluorophenyl, and 4-methoxyphenyl); Wollweber, H.; Hiltmann, R.; Stoepel, K; Kroneberg, H. G. *Eur. J. Med. Chem—Chim. Therapeutica* 1980, 15, 111–117 (specific examples of R³ being 3-methylphenyl, 4-methylphenyl, 3-methoxyphenyl, 4-chlorophenyl, and 3-chlorophenyl); Seibert, R. A.; Norton, T. R; Bensen, A. A.; Bergstrom, P. W. *J. Am. Chem. Soc.* 1946, 68, 2721–2723 (a specific example of R³ being quinolin-3-yl); Senear, A. B.; Sargent, H.; Mead, J. F.; Koepfli, J. B. *J. Am. Chem. Soc.* 1946, 68, 2695–2697 (a specific example of R³ being quinolin-4-yl). Amines of the formula F.5 may be prepared by procedures described by Shawe, T. T.; Koenig, G. J., Jr.; Ross, A. A. *Syn. Commun.* 1997, 27, 1777–1782 (a specific example of R³ being phenyl). Amines of the formula F.6 maybe prepared by procedures described by Crabb, T. A.; Hall, M. J. *J. Chem. Soc., Perkin Trans.* 2, 1974, 1419–1423 (a specific example of R¹ being phenyl). Amines of the formula F.7 may be prepared by procedures described by Ohnmacht, C. J., Jr.; McLeren, F. M. *J. Heterocyclic Chem.* 1991, 28, 1219–1224 (specific examples of R³ being phenyl, 4-methoxyphenyl, and 3-chloro-4-methoxyphenyl).

CHART F

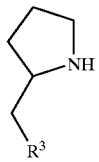

F.1

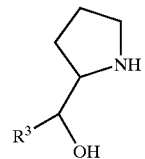

F.2

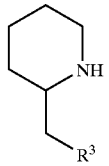

F.3

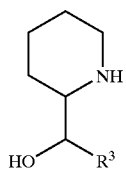

F.4

-continued

F.5
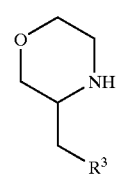

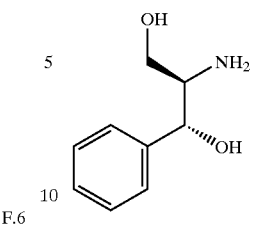
H.1

F.6
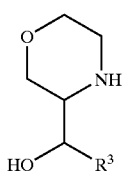

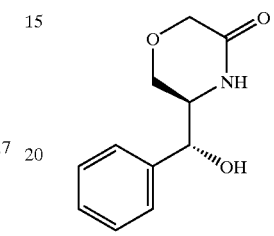
H.2

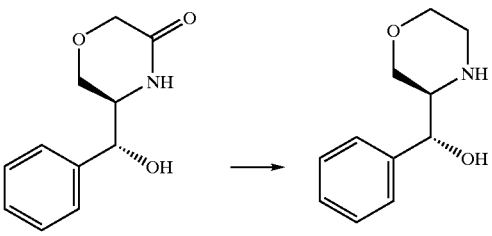
H.3

F.7
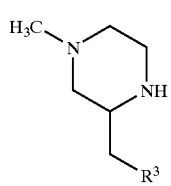

CHART H

Additional specific secondary amines described in Chart A of the formula H—W—B—R³ are prepared as described in Chart G. N-Boc-pyrrolidine (G.1) is metalated under the conditions described by Beak, P.; Lee, W. K. *J. Org. Chem.* 1993, 58, 1109–1117. The resulting anion is treated with aromatic or heteroaromatic carboxaldehydes (e.g. benzaldehyde) to afford the corresponding addition products (G.2). Deprotection employing common procedures (e.g. trifluoroacetic acid followed by neutralization) provides amino alcohols H—W—B—R³ of the formula G.3.

Additional specific secondary amines described in Chart A of the formula H—W—B—R³ are prepared as described in Chart I. The alcohol H.2 prepared in Chart H is treated with triphenylphosphine, dialkyl azodicarboxylate and 4-nitrobenzoic acid to afford the ester of formula I.1. The benzoate ester 1.1 is hydrolyzed with potassium carbonate in ethanol-dichloromethane to afford the lactam of formula I2. The amide of formula I2 is reduced with lithium aluminum hydride to afford the amino alcohol H—W—B—R³ of the formula I.3 which can be isolated as the hydrochloride salt.

CHART G

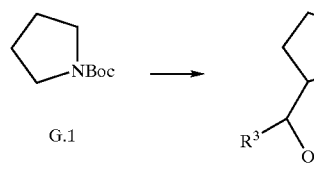

CHART I

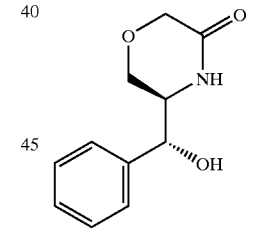
H.2

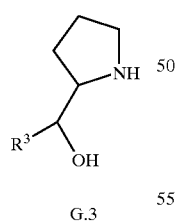
G.3

Additional specific secondary amines described in Chart A of the formula H—W—B—R³ are prepared as described in Chart H. R,R-2-Amino-1-phenyl-1,3-propane diol (H.1) is treated with metal alkoxide in an appropriate alcohol and methyl bromoacetate under conditions similar to those described by Crabb, T. A.; Hall, M. J. *J. Chem. Soc., Perkins Trans.* 2, 1974, 1419–1423. The resulting lactam (H.2) is reduced with lithium aluminum hydride to afford the amino alcohol H—W—B—R³ of the formula H.3 which can be isolated as the hydrochloride salt.

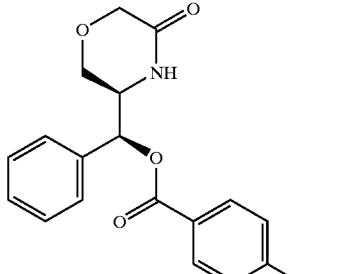
I.1

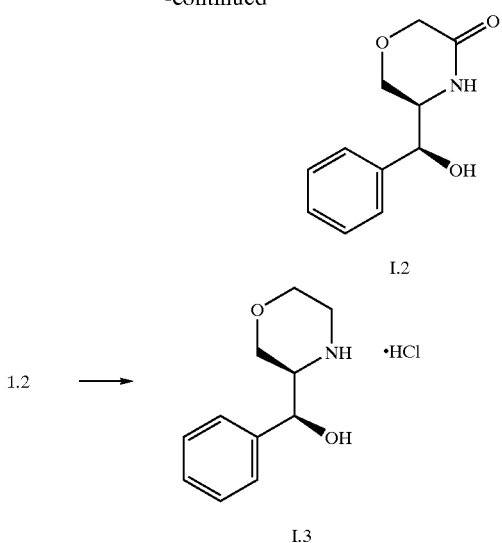

The compounds of Formula (I) may be prepared as single enantiomer or as a mixture of individual enantiomers which includes racemic mixtures. Methods to obtain preferentially a single enantiomer from a mixture of individual enantiomers or a racemic mixture are well known to those ordinarily skilled in the art of organic chemistry. Such methods include but are not limited to preferential crystallization of diastereomeric salts (e.g. tartrate or camphor sulfonate), covalent derivatization by a chiral, non-racemic reagent followed by separation of the resulting diasteromers by common methods (e.g. crystallization, chromatographic separation, or distillation) and chemical reversion to scalemic compound, Simulated Moving Bed technology, or high/medium-pressure liquid chromatography employing a chiral stationary phase (Eliel, E. L. *Stereochemistry of Organic Compounds,* 1994; Subramanian, G. *Chiral Separation Techniques: A Practical Approach,* 2001). These techniques may be performed on the final compounds of Formula (I) or on any intermediates to compounds of Formula (I) which bear a sterogenic center. Also, to facilitate separation by any of the methods described above, the compounds of Formula (I) or any intermediates to the compounds of Formula (1) which bear a stereogenic center may be transiently reacted with an achiral reagent, separated, and then reverted to scalemic compound by standard synthetic techniques.

It will be apparent to those skilled in the art that the described synthetic procedures are merely representative in nature and alternative synthetic processes are known to one of ordinary skill in organic chemistry.

The compounds of the present invention and pharmaceutically acceptable salts thereof are useful as antiviral agents. Thus, these compounds are useful to combat viral infections in mammals. Specifically, these compounds have anti-viral activity against the herpes virus, cytomegalovirus (CMV). These compounds are also active against other herpes viruses, such as the varicella zoster virus, the Epstein-Barr virus, the herpes simplex virus, and the human herpes virus type 8 (HHV-8).

The compounds of the present invention may also be useful for the treatment of several cardiovascular diseases such as atherosclerosis and restenosis. These diseases have been implicated with inflammation of coronary vessel walls resulting from infection or reactivation of herpesviruses.

The compounds of the present invention may also be useful for the treatment of herpesvirus infections in animals, for example, illnesses caused by bovine herpesvirus 1-5 (BHV), ovine herpesvirus 1 and 2, Canine herpesvirus 1, equine herpesvirus 1-8 (EHV), feline herpesvirus 1 (FHV), and pseudorabies virus (PRV).

Pharmaceutical Salts

The compound of formula I may be used in its native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a compound of the invention with a suitable acid affording a physiologically acceptable anion.

Routes of Administration

In therapeutic use for treating, or combining, viral infections in a mammal (i.e. human and animals) a compound of the present invention, its pharmaceutical compositions and other antiviral agents can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intraventricular injections or infusions techniques.

Topical administrations include the treatment of infectious areas dr organs readily accessibly by local application, such as, for example, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid parafin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injection, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer.

Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use. For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol ray use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions nay be formulated in an ointment such as petrolatum In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds ray be delivered using a sustained-release system. Various sustained-release materials have been established and are well known by those skilled in the art. Sustained-release capsules ray, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevention of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration.

Determination of a therapeutically effective amount is well within the capability of those skilled in the art. Generally, the quantity of active component will range between 0.5% to 90% by weight of the composition.

Generally, an antiviral effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the viral infection being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insulator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

Biological Data

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

The compounds of the present invention have shown activity in one or more of the assays described below. All of these assays are indicative of a compound's activity and thus of its use as an anti-viral agent.

The HCMV polymerase assay is performed using a scintillation proximity assay (SPA) as described in several references, such as N.D. Cook, et al., Pharmaceutical Manufacturing International, pages 49–53 (1992), K Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM MgCl$_2$, 0.36 mg/ml BSA, and 90 nM $^3$H-dTTP. Assays are run with and without CHAPS, (3-[(3-Cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μl/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25° C. or 37° C. H$_2$O bath and terminated via the addition of 40 μl/reaction of 0.5 M EDTA (pH 8) per well. Reactions are terminated within the time-frame during which substrate incorporation is linear and varied depending upon the enzyme and conditions used, I.e., 30 min. for HCMV polymerase. Ten (10) μl of streptavidin-SPA beads (20 mg/ml in PBS/10% glycerol) are added following termination of the reaction. Plates are incubated 10 min. at 37° C., then equilibrated to room temperature, and counted on a Packard Topcount. Linear regressions are performed and IC$_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM Dithiothreitol (DTT) is added to the polymerase buffer. Also, a different lot of CMV polymerase is used, which appears to be more active resulting in a more rapid polymerase reaction.

Results of the testing of compounds of the present invention in this assay are shown in Tables 1 below.

All results are listed as Polymerase IC$_{50}$(μM) values. In Table 1, the term "n.d." refers to activity data not determined.

TABLE 1

| Example | Polymerase IC$_{50}$ (μM) | | |
|---|---|---|---|
| | HCMV | HSV | VZV |
| 1 | 0.45 | 1.0 | 0.42 |
| 2 | 0.12 | 0.72 | 0.21 |
| 14 | 1.27 | 2.97 | nd |
| 15 | 0.024 | 0.022 | nd |

EXAMPLES

Preparation 1.

N-(4-Chlorobenzyl)-2-(chloromethyl)-7-methyl-4-oxo-4,7-dihydrothien [2,3-b]-pyridine-5-carboxamide.

N-(4-Chlorobenzyl)-2-(hydroxymethyl)-7-methyl-4-oxo-4,7-dihydrothieno[2,3-b]pyridine-5-carboxamide (3.00 g, prepared as described in U.S. Pat. No. 6,239,142) is dissolved in DMF (150 mL). DMAP (0.150 g), 2,4,6-collidine (2.73 mL), and methanesulfonyl chloride (1.60 mL) are added, and the reaction mixture is stirred at room temperature for 18 h. The reaction mixture is poured into water (300 mL). The resulting pale yellow solid is filtered off and triturated with acetonitrile to yield 2.75 g of the title compound. Physical characteristics: M.p. 250–256° C. (dec); $^1$H NMR (400 MHz, DMSOd-d$_6$) δ 10.48, 8.74, 7.58, 7.41-7.33, 5.16, 4.55, 3.97; $^{13}$C NMR (DMSO-d$_6$) δ 172.5, 164.5, 151.8, 146.4, 138.9, 135.7, 131.7, 130.5, 129.5, 128.7, 124.0, 115.0, 43.4, 41.8, 41.1; MS (EI) m/z 380 (M$^+$); HRMS (FAB) m/z 381.0255(M+H)$^+$. Anal. Found: C, 53.34; H, 3.70; N, 7.30; Cl, 17.91; S, 8.51.

Preparation 2.

2-(Hydroxy(phenyl)methyl)pyrrolidine.

N-Boc-pyrrolidine (5.0 g) is dissolved in diethyl ether (60 mL) and the solution is cooled to −78° C. N,N,N',N'-Tetramethylethylenediamine (TMEDA) (4.4 mL) is added to the mixture followed by sec-butyl lithium (27.0 mL, 1.3 M in cyclohexane) maintaining the temperature below 60° C. After 2 h, benzaldehyde (3.6 mL) is added and the mixture is stirred at −70° C. for an additional 30 mL The reaction mixture is allowed to warm to room temperature and is then quenched with water and poured into EtOAc (200 mL). The separated organic layer is washed with saturated aq. ammonium chloride (3×50 mL) followed by brine (50 mL), dried (MgSO$_4$), and concentrated. The crude product is purified by column chromatography (heptane/EtOAc, 8/1; 6/1) to afford 6.3 g of N-Boc-2-(hydroxy(phenyl)methyl)-pyrrolidine as a mixture of diasteromers. The resulting N-Boc-2-(hydroxy (phenyl)-methyl)pyrrolidine (5.6 g) is dissolved in dichloromethane (500 mL) and trifluoroacetic acid (60 mL) is added. The mixture is concentrated, dissolved in dichloromethane (200 mL), and washed with saturated aq. sodium bicarbonate (3×100 DL). The aqueous layers are extracted with dichloromethane (4×50 mL) and the combined organic layers are concentrated. The crude product is distilled in a Kugelrohr apparatus (150–175° C., 0.2 Torr) to afford 2.47 g of the title compound as a mixture of diasteromers. Physical characteristics. MS (ESI+) m/z 178 (M+H)$^+$.

Preparation 3.

Pyridin-2-yl(pyrrolidin-2-yl)methanol.

N-Boc-pyrrolidine (5.0 g) is dissolved in diethyl ether (60 mL) and the solution is cooled to −78° C. N,N,N',N'-Tetramethylenediamine (TMEDA) (4.4 mL) is added to the mixture followed by sec-butyl lithium (27.0 mL, 1.3 M in cyclohexane) maintaining the temperature below −60° C. After 2 h, 2-pyridine carboxaldehyde (3.3 mL) is added and the mixture is stirred at −70° C. for an additional 30 min. The reaction mixture is allowed to warm to room temperature and is then quenched with water (25 mL) and poured into EtOAc (250 mL). The separated organic layer is washed with water (2×50 mL) followed by brine (50 mL), dried (Na$_2$SO$_4$), and concentrated. The crude product is purified by column chromatography (heptane/EtOAc, 4/1; 2/1, 1/1) to afford 4.79 g of tert-butyl 2-(hydroxy(pyridin-2-yl) methyl)pyrrolidine-1-carboxylate as a mixture of diastereomers. The resulting alcohol is dissolved in dichloromethane (10 mL) and trifluoroacetic acid (80 mL) is added with ice bathe cooling. After 1 h, the reaction mixture is concentrated and added to 1 N sodium hydroxide solution (200 mL). The mixture is extracted with CH$_2$Cl$_2$ (3×100 mL). The combined organic layers are dried (Na$_2$SO$_4$) and concentrated. The resulting oil is distilled in a Kugelrohr apparatus (175–200° C., 0.2 Torr) to afford 2.04 g of the title compound as a mixture of diastereomers. Physical characteristics. $^1$H NMR (400 MHz, DMSO-d$_6$) δ 8.47, 7.76, 7.46, 7.24, 5.27, 4.50, 4.34, 3.32, 3.22, 2.83, 2.68, 1.62-1.36; MS (ESI+) m/z 179 (M+H)$^+$.

Preparation 4.

2-Furyl(pyrrolidin-2-yl)methanol.

N-Boc-pyrrolidine (5.0 g) is dissolved in diethyl ether (60 mL) and the solution is cooled to −78° C. N,N,N',N'-Tetramethylethylenediamine (TMEDA) (4.4 mL) is added to the mixture followed by sec-butyl lithium (27.0 mL, 1.3 M in cyclohexane) maintaining the temperature below −60° C. After 2 h, 2-furaldehyde (2.9 mL) is added and the mixture is stirred at −70° C. for an additional 30 min. The reaction mixture is allowed to warm to room temperature and is then quenched with water (25 mL) and poured into EtOAc (200 mL). The separated organic layer is washed with saturated aq. ammonium chloride (3×50 mL) followed by brine (50 mL), dried (MgSO$_4$), and concentrated The crude product is purified by column chromatography (heptane/EtOAc, 8/1; 5/1) to afford 4.97 g of 2-furyl(N-Boc-pyrrolidin-2-yl) methanol as a mixture of diasteromers. The resulting 2-furyl(N-Boc-pyrrolidin-2-yl)methanol (4.43 g) is dissolved in dichloromethane (200 mL) and trifluoroacetic acid (30 mL) is added. The mixture is poured into a 1 M solution of sodium hydroxide. The organic layer is separated and washed with saturated aq. sodium bicarbonate (2×100 mL). The aqueous layers are extracted with dichloromethane (4×50 mL) and the combined organic layers are concentrated. The crude product is purified by column chromatography (CH$_2$Cl$_2$/methanol/NH$_4$OH, 95/5/1; 90/10/1). The resulting oil is distilled in a Kugelrohr apparatus (0.175–200° C., 0.2 Torr) to afford 0.20 g of the title compound as a mixture of diastereomers. Physical characteristics. MS (ESI+) m/z 168 (M+H)$^+$.

Preparation 5.

(5R)-5-((R)-Hydroxy(phenyl)methyl)morpholin-3-one.

A dried flask under an atmosphere of nitrogen gas is charged with R-2-amino-1-phenyl-1,3-propane diol (10.1 g) and dry methanol (120 mL). The resulting solution is treated with sodium methoxide in methanol (25% wt, 30 mL) followed by dropwise addition of methyl bromoacetate (12.5 mL) via addition funnel. The resulting solution is heated to 65° C. for 8 hours. After cooling to room temperature, the reaction mixture is concentrated under reduced pressure. The residue is triturated with hot tetrahydrofuran (200 mL) and filtered. The filtered solid is triturated with hot tetrahydrofuran (50 mL) and re-filtered. The filtrates are combined and concentrated under reduced pressure. The resulting residue is adsorbed onto silica gel and purified by flash column chromatography (methanol/CH$_2$Cl$_2$, 1–6%) to obtain 0.7 g of the title compound. Physical characteristics. $^1$H NMR (400 MHz, DMSO-d$_6$) δ 7.90, 7.40–7.25, 5.75, 4.51, 4.03.8, 3.5–3.4, 3.4–3.20.

Preparation 6.

(R)(3R)-Morpholin-3-yl(phenyl)methanol hydrochloride.

(5R)-5-((R)-Hydroxy(phenyl)methyl)morpholin-3-one (Preparation 5, 0.63 g) is dissolved in dry tetrahydrofuran (12 mL) under an atmosphere of nitrogen gas. The solution is heated to 65° C. and treated dropwise with a solution of lithium alum hydride in tetrahydro an (1.0 M, 12 mL). After 8 hrs, the reaction is diluted with dry tetrahydrofuran (12 mL) and the temperature is maintained overnight. The reaction mixture is allowed to cool to room temperature and then cooled to 0° C. The reaction mixture is carefully quenched with water (0.25 mL), 15% aqueous sodium hydroxide (0.25 mL) and water (0.75 mL). The resulting mixture is allowed to warm to room temperature and filtered. The filtered solid is triturated with diethyl ether (3×25 mL). The tetrahydrofuran and diethyl ether filtrates are combined and concentrated under reduced pressure. The resulting residue is treated with methanol (10 mL) followed by a solution of HCl in methanol (1 N, 10 mL). The mixture is decanted and filtered through a plug of glass wool. The filtrate is concentrated under reduced pressure. The residue is dissolved in a small volume of methanol and treated with diethyl ether to afford a persistent cloudy suspension. The mixture is cooled overnight and the precipitant is collected, washed with small volumes of diethyl ether and hexanes, and finally dried in vacuo to afford 0.43 g of the title compound. Physical characteristics. M.p. 189–190° C.; $^1$H NMR (400 MHz, DMSO-d$_6$) δ 9.8, 9.1, 7.5–7.3, 6.46, 4.71, 4.52, 3.86, 3.73, 3.56, 3.4–3.3, 3.19, 3.05.

Preparation 7.

(S)((3R$^5$Oxomorpholin-3-yl)(phenyl)methyl 4-nitrobenzoate.

(5R)-5-((R)-Hydroxy(phenyl)methyl)morpholin-3-one (Preparation 5, 0.95 g), triphenylphosphine (1.78 g) and 4-nitrobenzoic acid (1.08 g) are treated with dry diethyl ether (45 mL) under an atmosphere of nitrogen gas. The mixture is cooled to 0° C. and treated dropwise with diethyl azodicarboxylate (1.0 mL). The reaction is allowed to slowly warm to room temperature overnight. The mixture is concentrated under reduced pressure, adsorbed onto silica gel and purified by flash column chromatography (1% methanol/ethyl acetate) to afford 1.2 g of the title compound. Physical characteristics. $^1$HNMR(400 MHz, CDCl$_3$) δ8.35–8.31, 8.26–8.22, 7,5–7.4, 6.04, 5.70, 4.3–4.1, 4.1–3.9.

Preparation 8.

(5R)-5-((S)-Hydroxy(phenyl)methyl)morpholin-3-one.

(S)-((3R)-5-Oxomorpholin-3-yl)(phenyl)methyl 4-nitrobenzoate (Preparation 7, 1.2 g) is treated with dichloromethane (10 mL), ethanol (30 mL) and potassium carbonate (1.0 g). After 2 h, the reaction mixture is filtered and the filtered solid is triturated with ethanol-dichloromethane (3:1 v:v, 3×30 mL). The filtrates are combined and concentrated under reduced pressure. The resulting residue is adsorbed onto silica gel and purified by flash column chromatography (methanol/CH$_2$Cl$_2$, 1–6%) to afford 0.61 g of the title compound. Physical characteristics. $^1$H NMR (400 MHz, DMSO-d$_6$) δ 7.55, 7.4–7.2, 5.65, 4.61, 3.92, 3.9–3.8, 3.65–3.55, 3.44.

Preparation 9.

(S)-(3R)-Morpholin-3-yl(phenyl)methanol hydrochloride.

(5R)-5-((S)-Hydroxy(phenyl)methyl)morpholin-3-one (Preparation 8, 0.51 g) is treated with dry tetrahydrofuran (20 mL) under an atmosphere of nitrogen gas. The solution is heated to 65° C. and treated dropwise with a solution of lithium aluminum hydride in tetrahydrofuran (1.0 M, 12 mL). The temperature is maintained overnight. The reaction mixture is allowed to cool to room temperature and then to 0° C. The reaction mixture is then carefully quenched with water (0.20 mL), 15% aqueous sodium hydroxide (0.20 mL) and water (0.60 mL). The resulting mixture is allowed to warm to room temperature, diluted with diethyl ether (25 mL) and filtered. The filtered solid is triturated with diethyl ether (3×25 mL). The tetrahydrofuran and diethyl ether filtrates are combined, dried over (Na$_2$SO$_4$), filtered and concentrated under reduced pressure. The resulting residue is treated with methanol (10 mL) followed by HCl in methanol (1.25 N, 10 mL). The mixture is decanted and the filtrate is concentrated under reduced pressure. The residue is dissolved in a small volume of methanol and treated with diethyl ether to afford a persistent cloudy suspension. The mixture is cooled overnight and the precipitant is collected, washed with small volumes of diethyl ether and hexanes, and finally dried in vacuo to afford 0.11 g of the title compound. Physical characteristics. $^1$H NMR (400 MHz, DMSO-d$_6$) δ 9.6, 9.0, 7.5–7.3, 6.33, 5.00, 4.52, 3.9–3.8, 3.7–3.4, 3.2–3.1.

Example 1

2-(((3S)-3-Benzylmorpholin-4-yl)methyl)-N-(4-chlorobenzyl)-7-methyl-4-oxo-4,7-dihydrothieno[2,3-b]pyridine-5-carboxamide.

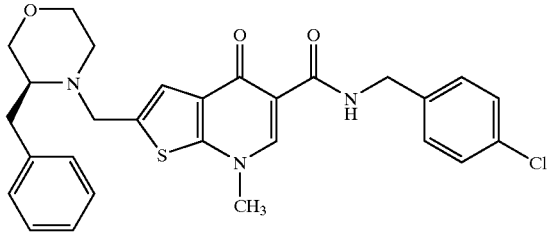

N-(4-Chlorobenzyl)-2-(chloromethyl)-7-methyl-4-oxo-4,7-dihydrothieno[2,3-b]pyridine-5-carboxamide (Preparation 1, 100 mg) and diisopropylethylamine (0.13 mL) is added to a mixture of (S)-3-(phenylmethyl)morpholine (93 mg, prepared as described by Shawe, T. T. *Syn. Comm.* 1997,27, 1777–1782) in DMF (5 mL). The mixture is heated at 90° C. for 3 hours. After cooling to room temperature, the solution is poured into CH$_2$Cl$_2$ (125 mL) and washed with water (2×100 mL). The organic layer is dried (Na$_2$SO$_4$) and the solution filtered. Evaporation of the solvent gives a residue which is purified by column chromatography (methanol/ CH$_2$Cl$_2$, 0–6%) to obtain 80 mg of the title compound. Physical characteristics. $^1$H NMR (400 MHz, DMSO-d$_6$) δ 10.61, 8.71, 7.41–7.20, 4.54, 4.20, 3.96, 3.91, 3.59, 3.41, 3.20, 2.89, 2.82–2.66, 2.40; MS (ESI+) m/z 522 (M+H).

Example 2

N-(4-Chlorobenzyl)-2-(((2R*2)-(S*)-hydroxy(phenyl) methyl)pyrrolidin-1-yl)methyl)-7-methyl-4-oxo-4,7-dihydrothieno[2,3-b]pyridine-5-carboxamide.

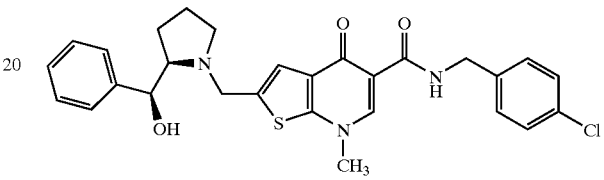

N-(4-Chlorobenzyl)-2-(chloromethyl)-7-methyl-4-oxo-4, 7-dihydrothieno[2,3-b]pyridine-5-carboxamide (Preparation 1, 500 mg) is dissolved in DMF (24 mL). Diisopropylethylamine (0.46 mL) is added to the mixture followed by a solution of 2-(hydroxy(phenyl)methyl)pyrrolidine (Preparation 2, 0.47 g) in DMF (4 mL). The mixture is heated to 90° C. for 2 h and then allowed to cool to room temperature. The reaction mixture is poured into water (60 mL) and extracted with EtOAc (3×50 mL). The combined organic layers are washed with water (2×25 mL) and brine (25 mL), dried (Na$_2$SO$_4$), and concentrated. The crude product is purified by column chromatography (CH$_2$Cl$_2$/ methanol, 100/1; 50/1; 33/1) to afford 93 mg of the tide compound as the less polar diastereomer. Physical characteristics. M.p. 158–162° C.; $^1$H NMR (400 MHz DMSO-d$_6$) δ 10.61, 8.70, 7.42–7.20, 5.02, 4.54, 4.52, 3.96, 3.73, 3.60, 2.90, 2.83, 2.30, 1.85, 1.61; MS (ESI+) m/z 522 (100, (M+H)$^+$), 523 (25), 524 (36).

Example 3

N-(4-Chlorobenzyl)-2-(((2R*)-2-((R*)hydroxy(pyridin-2-yl)methyl)pyrrolidin-1-yl)methyl)-7-methyl-4-oxo-4,7-dihydrothieno[2,3-b]pyridine-5-carboxamide.

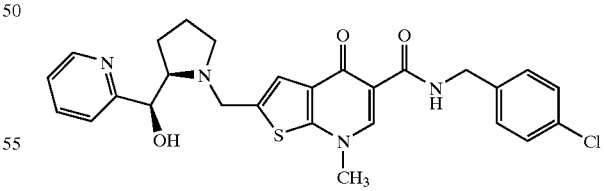

Analogous to the procedures described in Example 2, N-(4-Chlorobenzyl)-2-(chloromethyl)-7-methyl-4-oxo-4,7-dihydrothieno[2,3-b]pyridine-5-carboxamide (Preparation 1) is treated with pyridin-2-yl(pyrrolidin-2-yl)methanol (Preparation 3) to afford the title compound. Physical characteristics. $^1$H NMR (400 MHz, DMSO-d$_6$) δ 10.62, 8.70, 8.50, 7.78, 7.54, 7.41–7.33, 7.30, 7.24, 5.13, 4.67, 4.55, 4.04, 3.96, 3.73, 3.15–3.10, 2.94–2.86, 2.33–2.27, 1.84–1.77, 1.64–1.46; MS (ESI+) m/z 523 (M+H)$^+$.

Example 4

N-(4-Chlorobenzyl)-2-(((2R*)-2-((R*)-2-furyl(hydroxy)methyl)pyrrolidin-1-yl)-methyl)-7-methyl-oxo-4,7-dihydrothieno[2,3-b]pyridine-5-carboxamide.

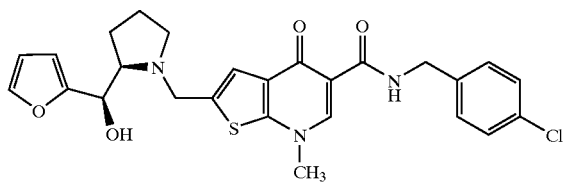

Analogous to the procedures described in Example 2, N-(4-Chlorobenzyl)-2-(chloromethyl)-7-methyl-4-oxo-4,7-dihydrothieno[2,3-b]pyridine-5-carboxamide (Preparation 1) is treated with 2-furyl(pyrrolidin-2-yl)methanol (Preparation 4) to afford the title compound Employing procedures analogous to those described in Example 2 and utilizing the appropriate amino alcohol, Examples 5–13 are prepared. The corresponding amino alcohols are prepared according to procedures described in Tsutsumi, S.; Okonogi, T; Shibahara, S.; Ohuchi, S.; Hatsushiba, E.; Patchett, A. A.; Christensen, B. G. *J. Med. Chem.* 1994, 37, 3492–3502 starting from (R)-N-Boc-prolinal or (R)-N-alloc-prolinal as follows, (2R)-2-(R)-hydroxy(1,3-thiazol-2-yl)methyl)pyrrolidine (Example 5); (2R)-2-((R)-hydroxy(thien-2-yl)methyl)pyrrolidine (Example 6); (2R)-2-((R)-1,3-benzothiazol-2-yl(hydroxy)methyl)pyrrolidine (Example 7); (2R)-2-((R)-hydroxy(1,3-thiazol-5-yl)methyl)pyrrolidine (Example 8); (2R)-2-((R)-hydroxy(pyridin-2-yl)methyl)pyrrolidine (Example 9); (2R)-2-((S)-hydroxy(pyridin-3-yl)methyl)pyrrolidine (Example 10); (2R)-2-((S)-hydroxy(pyrimidin-5-yl)methyl)-pyrrolidine (Example 11); (2R)-2-(R)-hydroxy(1H-imidazol-2-yl)methyl)pyrrolidine (Example 12); and (2R)-2-((R)-1,3-benzoxazol-2-yl(hydroxy)methyl)pyrrolidine (Example 13).

Example 5

N-(4-Chlorobenzyl)-2-(((2R)-2-((R)-hydroxy(1,3-thiazol-2-yl)methyl)pyrrolidin-1-yl}methyl)-7-methyl-4-oxo-4,7-dihydrothieno[2,3-b]pyridine-5-carboxamide.

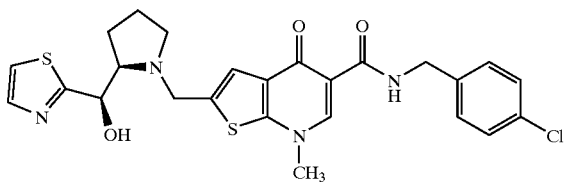

Physical characteristics. MS (ESI+) m/z 529 (M+H)+.

Example 6

N4-Chlorobenzyl)-2-(((2R)-2-((R)-hydroxy(thien-2-yl)methyl)pyrrolidin-1-yl}methyl)-7-methyl-4-oxo-4,7-dihydrothieno[2,3b]pyridine-5-carboxamide.

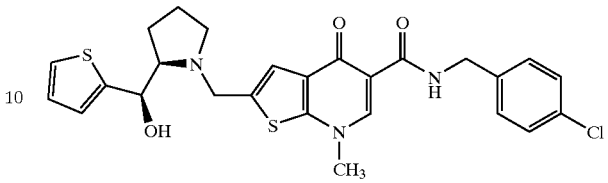

Physical characteristics. MS (ESI+) m/z 528 (M+H)+.

Example 7

2-(((2R)-2-((R)-1,3-Benzothiazol-2-yl(hydroxy)methyl)pyrrolidin-1-yl)methyl)-N-(4-chlorobenzyl)-7-methyl-4-oxo-4,7-dihydrothieno[2,3-b]pyridine-5-carboxamide.

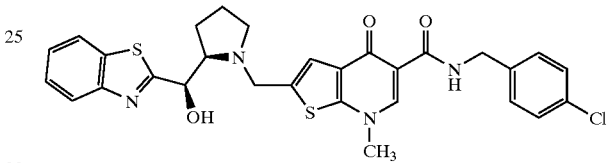

Physical characteristics. MS (ESI+) m/z 579 (M+H)+.

Example 8

N-(4-Chlorobenzyl)-2-(((2R)-2-((R)-hydroxy(1,3-thiazol-5-yl)methyl)pyrrolidin-1-yl)methyl)-7-methyl-4-oxo-4,7-dihydrothieno[2,3-b]pyridine-5-carboxamide.

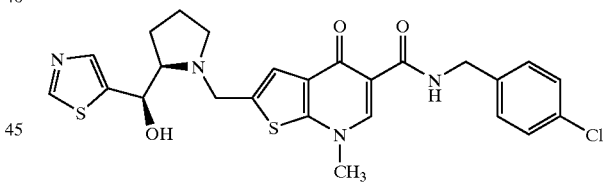

Physical characteristics. MS (ESI+) m/z 529 (M+H)4.

Example 9

N-(4-Chlorobenzyl)-2-(((2R)-2-((R)-hydroxy(pyridin-2-yl)methyl)pyrrolidin-1-yl)methyl)-7-methyl-4-oxo-4,7-dihydrothieno[2,3-b]pyridine-5-carboxamide.

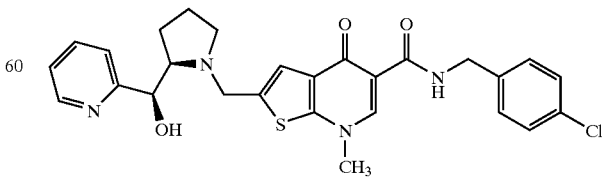

Physical characteristics. MS (ESI+) m/z 523 (M+H)+.

Example 10

N-(4-Chlorobenzyl)-2-(((2R)-2-((hydroxy(pyridin-3-yl)methyl)pyrrolidin-1-yl)methyl)-7-methyl-4-oxo-4,7-dihydrothieno[2,3-b]pyridine-5-carboxamide.

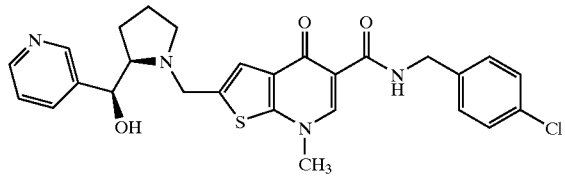

Physical characteristics. MS (ESI+) m/z 523 (M+H)$^+$.

Example 11

N-(4-Chlorobenzyl)-2-(((2R)-2-((S)-hydroxy(pyrimidin-5-yl)methyl)pyrrolidin-1-yl)methyl)-7-methyl-4-oxo-4,7-dihydrothieno[2,3-b]pyridine-5-carboxamide.

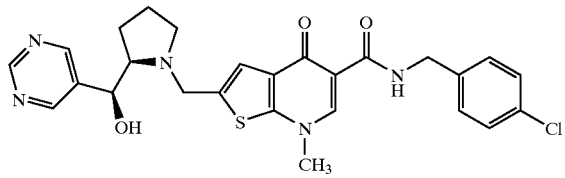

Physical characteristics. MS (ESI+) m/z 524 (M+H)$^+$.

Example 12

N-(4-Chlorobenzyl)-2-(((2R)-2-((R)-hydroxy(1H-imidazol-2-yl)methyl)pyrrolidin-1-yl)methyl)-7-methyl-oxo-4,7-dihydrothieno[2,3-b]pyridine-5-carboxamide.

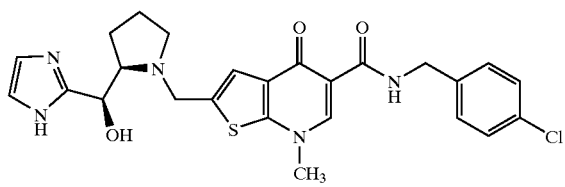

Physical characteristics. MS (ESI+) m/z 512 (M+H)$^+$.

Example 13

2-(((2R)-2-((R)-1,3-Benzoxazol-2-yl(hydroxy)methyl)pyrrolidin-1-yl)methyl)-N-(4-chlorobenzyl)-7-methyl-4-oxo-4,7-dihydrothieno[2,3-b]pyridine-5-carboxamide.

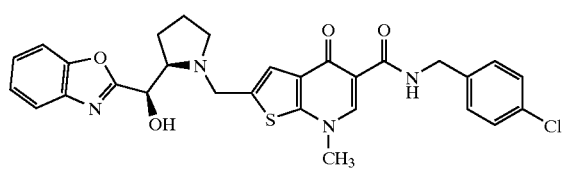

Physical characteristics. MS (ESI+) m/z 563 (M+H)$^+$.

Example 14

N-(4-Chlorobenzyl)-2-(((3R)-3-((R)-hydroxy(phenyl)methyl)morpholin-4-yl)-methyl)-7-methyl-4-oxo-4,7-dihydrothieno[2,3-b]pyridine-5-carboxamide

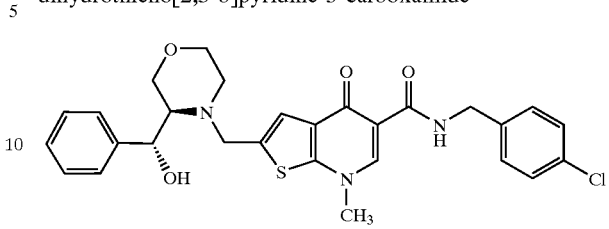

N-(4-Chlorobenzyl)-2-(chloromethyl)-7-methyl-4-oxo-4,7-dihydrothieno[2,3-b]pyridine-5-carboxamide (Preparation 1, 134 mg) and (R)-(3R)-morpholin-3-yl(phenyl)methanol hydrochloride (Preparation 6, 112 mg) in DMF (3 mL) is treated with diisopropylethylamine (0.5 mL). The mixture is heated at 95° C. overnight. After cooling to room temperature, the solution is poured into ethyl acetate (75 mL) and washed with dilute pH 4 phosphate buffer (25 mL), dilute pH 7 phosphate buffer (2×25 mL), and brine (25 mL). The organic layer is dried (Na$_2$SO$_4$), filtered and concentrated under reduced pressure. The resulting residue is purified by flash column chromatography (methanol/CH$_2$Cl$_2$, 1–3%) and ethyl acetate-hexanes crystallization to afford 0.15 g of the title compound. Physical characteristics. M.p. 171–172° C.; $^1$H NMR(400 MHz, DMSO-d$_6$) δ 10.63, 8.71, 7.4–7.3, 7.3, 5.42, 5.09, 4.55, 4.50, 4.15, 3.97, 3.5, 3.4, 3.04, 2.9, 2.8, 2.4; HRMS m/z 538.1558 (M+H)$^+$. Anal. Found. C, 62.41; H, 5.17; N, 7.73.

Example 15

N-(4-Chlorobenzyl)-2-(((3R)-3-((S)hydroxy(phenyl)methyl)morpholin-4-yl)-methyl)-7-methyl-4-oxo-4,7-dihydrothieno[2,3-b]pyridine-5-carboxamide

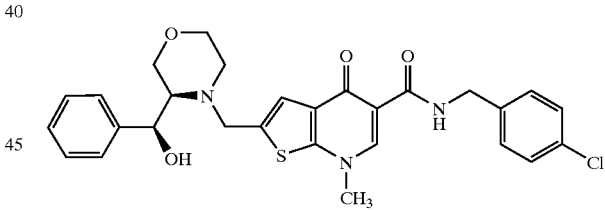

N-(4-Chlorobenzyl)-2-(chloromethyl)-7-methyl-4-oxo-4,7-dihydrothieno[2,3-b]pyridine-5-carboxamide (Preparation 1, 134 mg) and (S)-(3R)-morpholin-3-yl(phenyl)methanol hydrochloride (Preparation 9, 111 mg) in DMF (3 mL) is treated with diisopropylethylamine (0.5 mL). The mixture is heated at 90° C. overnight. After cooling to room temperature, the solution is poured into ethyl acetate (75 mL) and washed with dilute pH 4 phosphate buffer (10 mL), dilute pH 7 phosphate buffer (10 mL), and brine (10 mL). The organic layer is dried (Na$_2$SO$_4$), filtered and concentrated under reduced pressure. The resulting residue is purified by flash column chromatography (methanol/CH$_2$Cl$_2$, 1–3%) and ethyl acetate-hexanes crystallization to afford 0.13 g of the title compound Physical characteristics. M.p. 129–134° C.; $^1$H NMR (400 MHz, DMSO-d$_6$) δ 10.60, 8.67, 7.41–7.25, 5.33, 5.07, 4.54, 4.17, 3.88, 3.81, 3.73, 3.6, 3.5–3.4, 2.94, 2.6, 2.4–2.3; HRMS m/z 538.1561 (M+H)$^+$. Anal. Found: C, 62.33; H, 5.25; N, 7.75.

Preparation 10.

N-(4-Chlorobenzyl)-7-ethyl-2-(hydroxymethyl)-4-oxo-4,7-dihydrothieno[2,3-b]-pyridine-5-carboxamide.

Potassium carbonate (0.87 g) and iodoethane (0.5 mL) are added to a solution of N-(4-chlorobenzyl)-4-hydroxy-2-(hydroxymethyl)thieno[2,3-b]pyridine-5-carboxamide (2.0 g, prepared as described in U.S. Pat. No. 6,239,142) in anhydrous DMF (60 mL). The reaction mixture is stirred at room temperature for 18 h. The mixture is diluted with water (150 mL) and filtered. The resulting white powder is washed with water (15 mL) followed by diethyl ether (15 mL) and dried in a vacuum oven to afford 1.64 g of the title compound as a white solid. Physical characteristics. M.p. 169–172° C.; $^1$H NMR (300 MHz, DMSO-$d_6$) δ 10.65, 8.74, 7.37, 7.29, 5.81, 4.70, 4.54, 4.32, 1.44. HRMS (FAB) m/z 377.0720 (M+H)$^+$. Anal. Found. C, 56.87; H, 4.77; N, 7.38; Cl, 9.35; S, 8.44.

Preparation 11.

N-(4-Chlorobenzyl)-2-(chloromethyl)-7-ethyl-4-oxo-4,7-dihydrothieno[2,3-b]-pyridine-5-carboxamide.

4-N,N-Dimethylaminopyridine (80 mg), 2,4,6-collidine (1.41 mL), and methanesulfonyl chloride (0.83 mL) are added to a solution of N-(4-chlorobenzyl)-7-ethyl-2-hydroxymethyl)-4-oxo-4,7-dihydrothieno[2,3-b]pyridine-5-carboxamide (Preparation 10., 1.61 g) in anhydrous DMF (80 mL). The reaction mixture is stirred at room temperature for 24 h The mixture is diluted with water (150 mL) and filtered. The resulting white powder is recrystallized from acetonitrile and dried in a vacuum oven to afford 1.4 g of the title compound as a white solid. Physical characteristics. M.p. 199–200° C.; $^1$H NMR (300 MHz, DMSO-$d_6$) δ 10.45, 8.77, 7.57, 7.38, 5.15, 4.54, 4.32, 1.44. Anal. Found: C, 54.53; H, 3.94; N, 7.03; Cl, 17.57; S, 8.09.

Example 16

N-(4-Chlorobenzyl)-7-ethyl-2-(((2R*)-2-((S*)-hydroxy (phenyl)methylpyrrolidine-1-yl)methyl)-4-oxo-4,7-dihydrothieno[2,3-b]pyridine-5-carboxamide.

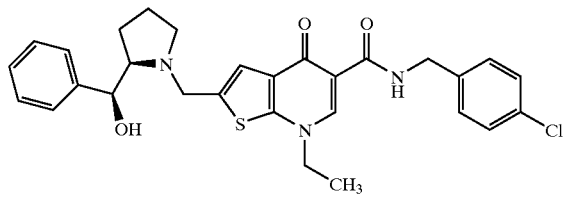

Analogous to the procedures described in Example 2, N-(4-chlorobenzyl)-2-(chloromethyl)-7-ethyl-4-oxo-4,7-dihydrothieno[2,3-b]pyridine-5-carboxamide (Preparation 11) is treated with 2-hydroxy(phenyl)methyl)pyrrolidine (Preparation 2) to afford the title compound.

Example 17

N-(4-Chlorobenzyl-7-ethyl-2-(((3R)-3-((S)-hydroxy (phenyl)methyl)morpholin-4-yl)methyl)-4-oxo-4,7-dihydrothieno[2,3-b]pyridine-5-carboxamide.

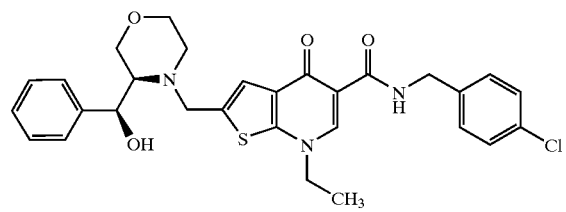

Analogous to the procedures described in Example 15, N-(4-chlorobenzyl)-2-(chloromethyl)-7-ethyl-4-oxo-4,7-dihydrothieno[2,3-b]pyridine-5-carboxamide (Preparation 11) is treated with (S)-(3R)-morpholin-3-yl(phenyl) methanol hydrochloride (Preparation 9) to afford the title compound.

Preparation 12.

N-(4-Chlorobenzyl)-7-propyl-2-(hydroxymethyl)-4-oxo-4,7-dihydrothieno[2,3-b]-pyridine-5-carboxamide.

Potassium carbonate (0.91 g) and 1-iodopropane (0.64 mL) are added to a solution of N-(4-chlorobenzyl)-4-hydroxy-2-(hydroxymethyl)thieno[2,3-b]pyridine-5-carboxamide (2.0 g, prepared as described in U.S. Pat. No. 6,239,142) in anhydrous DMF (60 mL). The reaction mixture is stirred at room temperature for 4 h. The mixture is diluted with water (150 mL) and filtered. The resulting white powder is washed with water (15 mL) followed by diethyl ether (15 mL) and dried in a vacuum oven to afford 1.73 g of the title compound as a white solid Physical characteristics. Mp 174–175° C. $^1$H NMR (300 MHz, DMSO-$d_6$) δ 10.62, 8.72, 7.38, 7.29, 5.80, 4.69, 4.55, 4.27, 1.87, 0.89; Anal. Found: C, 58.20; H, 4.96; N. 7.13; Cl, 8.98; S, 8.16.

Preparation 13.

N-(4-Chlorobenzyl)-2-(chloromethyl)-7-propyl-4-oxo-4,7-dihydrothieno[2,3-b]-pyridine-5-carboxamide.

4-N,N-Dimethylaminopyridine (80 mg), 2,4,6-collidine (1.39 mL), and methanesulfonyl chloride (0.81 mL) are added to a solution of N-(4-chlorobenzyl)-7-propyl-2-(hydroxymethyl)-4-oxo-4,7-dihydrothieno[2,3-b]pyridine-5-carboxamide (Preparation 12, 1.63 g) in anhydrous DMF (80 mL). The reaction mixture is stirred at room temperature for 24 h. The mixture is diluted with water (150 mL) and filtered. The resulting light yellow powder is recrystallized from acetonitrile and dried in a vacuum oven to afford 1.4 g of the title compound as a light yellow solid. Physical characteristics. Mp 186.5–188° C.; $^1$H NMR (300 Mhz,7 DMSO-6) δ 10.45, 8.75, 7.56, 7.39, 5.15, 4.54, 4.27, 1.85, 0.91. Anal. Found: C, 55.76; H, 4.59; N, 6.95; Cl, 16.88; S, 7.80.

Example 18
N-(4-Chlorobenzyl)-2-(((2R*)-2-((S*)-hydroxy(phenyl)methyl)pyrrolidin-1-yl)methyl)-4-oxo-7-propyl-4,7-dihydrothieno[2,3-b]pyridine-5-carboxamide.

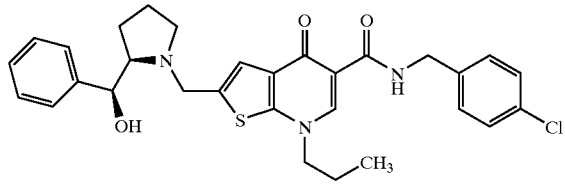

Analogous to the procedures described in Example 2, N-(4-chlorobenzyl)-2-(chloromethyl)-7-propyl-4-oxo-4,7-dihydrothieno[2,3-b]pyridine-5-carboxamide (Preparation 13) is treated with 2-hydroxy(phenyl)methyl)pyrrolidine (Preparation 2) to afford the title compound.

Example 19
N-(4-Chlorobenzyl)-2-(((3R)-3-((S)-hydroxy(phenyl)methyl)morpholin-4-yl)methyl)-4-oxo-7-propyl-4,7-dihydrothieno[2,3-b]pyridine-5-carboxamide.

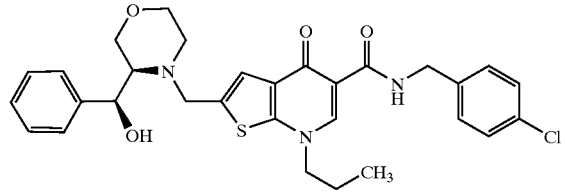

Analogous to the procedures described in Example 15, N-(4-chlorobenzyl)-2-(chloromethyl-7-propyl-4-oxo-4,7-dihydrothieno[2,3-b]pyridine-5-carboxamide (Preparation 13) is treated with (S)-(3R)-morpholin-3-yl(phenyl)methanol hydrochloride (Preparation 9) to afford the title compound.

Preparation 14.
N-(4-Chlorobenzyl)-2-(hydroxymethyl)-7-(2-methoxyethyl)-4-oxo-4,7-dihydro-thieno[2,3-b]pyridin-5-carboxamide.

Potassium carbonate (5.0 g) and bromoethylmethyl ether (5.0 g) are added to a solution of N-(4-chlorobenzyl)-4-hydroxy-2-(hydroxymethyl)thieno[2,3-b]pyridine-5-carboxamide (11.4 g, prepared as described in U.S. Pat. No. 6,239,142) in anhydrous DMF (350 mL). The reaction mixture is stirred at room temperature for 18 b. The mixture is diluted with water (600 mL) and filtered. The resulting white powder is dried in a vacuum oven to afford 8.44 g of the title compound as a white solid. Physical characteristics. M.p. 193° C.; $^1$H NMR (300 MHz, DMSO-$d_6$) δ 10.58, 8.65, 7.37, 7.29, 5.82, 4.70, 4.54, 4.47, 3.76, 3.24. HRMS (FAB) m/z 407.0836 (M+H)$^+$. Anal. Found: C, 55.81; H, 4.71; N, 6.90; Cl, 8.58, S, 7.81.

Preparation 15.
N-(4-Chlorobenzyl)-2-(chloromethyl-7-(2-methoxyethyl)-4-oxo-4,7-dihydro-thieno[2,3-b]pyridine-5-carboxamide.

4-N,N-dimethylaminopyridine (360 mg), 2,4,6-collidine (6.5 mL), and methanesulfonyl chloride (3.8 mL) are added to a solution of N-(4-chlorobenzyl)-2-(hydroxymethyl)-7-(2-methoxyethyl)-4-oxo-4,7-dihydrothieno[2,3-b]pyridine-5-carboxamide (Preparation 14, 8.0 g) in anhydrous DMF (360 mL). The reaction mixture is stirred at room temperature for 18 h. The mixture is diluted with water (600 mL) and filtered The resulting off-white powder is dried in a vacuum oven to afford 7.03 g of the title compound as an off-white solid. Physical characteristics. M.p. 192–193° C.; $^1$H NMR (300 MHz, DMSO-$d_6$) δ 10.48, 8.67, 7.55, 7.37, 5.14, 4.53, 4.46, 3.74, 3.24; HRMS (FAB) m/z 425.0480 (M+H)$^+$. Anal. Found. C, 53.38, H 4.37; N, 6.66; Cl, 15.77; S, 7.69.

Example 20
N-(4-Chlorobenzyl)-2-(((2R*)-2-((S*)-hydroxy(phenylmethyl)pyrrolidin-1-yl)-methyl)-7-(2-methoxyethyl)-4-oxo-4,7-dihydrothieno[2,3-b]pyridine-5-carboxamide.

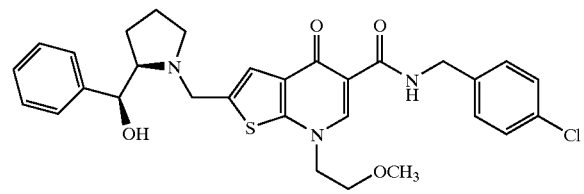

Analogous to the procedures described in Example 2, N-(4-chlorobenzyl)-2-(chloromethyl)-7-(2-methoxyethyl)-4-oxo-4,7-dihydrothieno[2,3-b]pyridine-5-carboxamide (Preparation 15) is treated with 2-(hydroxy(phenyl)methyl)pyrrolidine (Preparation 2) to afford the title compound.

Example 21
N-(4-Chlorobenzyl)-2-(((3R)-3-((hydroxy(phenyl)methyl)morpholin-4-yl)-methyl)-7-(2-methoxyethyl)-4-oxo-4,7-dihydrothieno[2,3-b]pyridine-5-carboxamide.

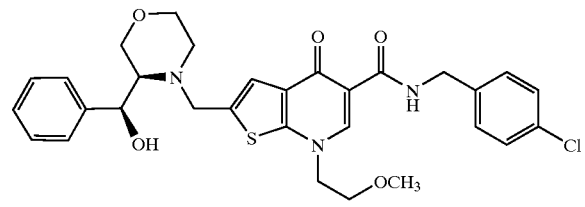

Analogous to the procedures described in Example 15, N-(4-chlorobenzyl)-2-(chloromethyl)-7-(2-methoxyethyl)-4-oxo-4,7-dihydrothieno[2,3-b]pyridine-5-b-carboxamide (Preparation 15) is treated with (S)-(3R)-morpholin-3-yl (phenyl)methanol hydrochloride (Preparation 9) to afford the title compound.

Preparation 16.
4-Bromo-5-chloro-2-thiophenocarbaldehyde.

n-Butyl lithium (2.5 M in hexanes, 105 mL) is slowly added to a solution of diisopropylamine (36.8 mL) in THF (600 mL) at 0° C. After 15 min, the mixture is cooled to –70° C. A solution of 3-bromo-2-chlorothiophene (49.4 g) in THF (20 mL) is added maintaining the internal temperature below –65° C. After 15 min, DMF (25.2 mL) is added. The mixture is stirred at –70° C. for 15 min and then allowed to warm to room temperature. The reaction mixture is quenched with saturated aq. NH$_4$Cl solution (200 mL) and concentrated in vacuo to one-half volume. The residue is diluted with EtOAc (500 mL) and the aqueous layer is separated. The aqueous layer is extracted with EtOAc (2×100 mL). The combined organic layers are washed with brine (100 mL), dried (MgSO$_4$), and concentrated to afford an oil. The oil is purified by column chromatography (heptane; heptane/EtOAc, 20/1; 10/1). After concentration the resulting solid is suspended in heptane (75 mL) and filtered to afford 30.3 g of the title compound as a light yellow solid. Physical characteristics. M.p. 61–62° C.; $^1$H NMR (300 MHz, DMSO-d$_6$) δ 9.82, 8.14; $^{13}$C NMR (100 MHz, CDCl$_3$) δ 181.6, 140.9, 138.5, 138.1, 112.8. Anal. Found: C, 26.68; H, 0.91; Br, 35.11; Cl, 15.78; S, 14.17.

Preparation 17.

4-((4-Bromo-5-chloro-2-thienyl)methyl)morpholine.

Morpholine (15.2 mL), acetic acid (9.1 mL), and then sodium triacetoxy-borohydride (50.3 g) is added to a solution of 4-bromo-5-chloro-2-thiophene-carbaldehyde (Preparation 16, 35.7 g) in 1,2-dichloroethane (600 mL) at 0° C. The mixture is allowed to warm to room temperature, and after 18 h, it is quenched with a 2N NaOH solution (200 mL) with ice bath cooling. The organic layer is separated and washed with a 1N NaOH solution (2×200 mL). The combined aqueous layers are extracted with CH$_2$Cl$_2$ (2×100 mL). The combined organic layers are extracted with 0.25 M HCl solution (4×500 mL) and the resulting aqueous layer is made basic with 2N NaOH solution. The mixture is then extracted with CH$_2$Cl$_2$ (4×500 mL) and the organic layer is dried (Na$_2$SO$_4$) and concentrated to afford 39.24 g of the title compound as a light yellow oil. Physical characteristics. $^1$H NMR (400 MHz, DMSO-d$_6$) δ 7.03, 3.63, 3.57, 2.42; $^3$C NMR (100 MHz, CDCl$_3$) δ 140.9, 127.3, 125.9, 109.2, 66.9, 57.6, 53.3; MS (ESI+) m/z 296 (M+H)$^+$. Anal. Found: C, 36.49; H, 3.77; N, 4.70; Br, 26.73; Cl, 12.06; S, 10.72.

Preparation 18.

1-(2-Chloro-5-(morpholin-4-methyl)thien-3-yl)ethanone.

4-((4-Bromo-5-chloro-2-thienyl)methyl)morpholine (Preparation 17, 44.5 g) is dissolved in diethyl ether (600 mL) and the solution is cooled to −70° C. n-Butyl lithium (2.5 M in hexanes, 66 mL) is added slowly maintaining the temperature below −65° C. The mixture is stirred at −70° C. for 15 min and then a solution of N-methoxy-N-methylacetamide (18.6 g) in diethyl ether (20 mL) is added maintaining the temperature below 60° C. After 10 min, the mixture is allowed to warm to room temperature and to stir for 18 h. The reaction mixture is then quenched with saturated aq. NH$_4$Cl (250 mL) followed by saturated aq. NaHCO$_3$ (200 mL). The mixture is extracted with EtOAc (4×200 mL). The combined organic layers are washed with brine (2×100 mL), dried (Na$_2$SO$_4$), and concentrated. The crude product is purified by column chromatography (heptane/acetone, 8/1) to afford 25.66 g of the title compound as a yellow oil. Physical characteristics. $^1$H NMR (400 MHz, DMSO-d$_6$)δ 7.33, 3.63, 3.58, 2.51, 2.42; MS (ESI+) m/z 260 (M+H)$^+$.

Preparation 19.

Ethyl 3-(2-Chloro-5-(morpholin 4 ylmethyl)thien-3-yl)-3-oxopropanoate.

Sodium hydride (60% dispersion in mineral oil, 16.7 g) is added to a cold (0° C.) solution of 1-(2-chloro-5-morpholin-4-ylmethyl)thien-3-yl)ethanone (Preparation 18, 54.37 g) in diethylcarbonate (420 mL). The reaction mixture is allowed to warm to room temperature. After 1 h, the mixture is carefully warmed to 40° C. resulting in a vigorous exotherm causing the temperature to rise to 95° C. The mixture is allowed to cool to room temperature and is then quenched with glacial acetic acid (20 mL). The reaction mixture is diluted with water (350 mL) and saturated aq. Na$_2$CO$_3$ (200 mL), and the solution is extracted with MTBE (4×250 mL). The combined organic layers are washed with saturated aq. NaHCO$_3$ (50 mL) followed by brine (2×100 mL), dried (Na$_2$SO$_4$), and concentrated to provide an oil. The crude product is purified by column chromatography (heptane/acetone, 8/1; 5/1) to afford 51.7 g of the title compound as a yellow oil. Physical characteristics. $^1$H NMR (400 MHz, DMSO-d$_6$) δ 12.45, 7.36, 7.25, 5.76, 4.22, 4.11, 4.04, 3.64, 3.58, 2.42, 1.26, 1:18; MS (ESI+) m/z 332 (M+H)$^+$.

Preparation 20.

N-(4-Chlorobenzyl)-3-(2-chloro-5-(morpholin-4-ylmethyl)thien-3-yl)-3-oxo-propanamide.

A solution of ethyl 3-(2-chloro-5-morpholin-4-ylmethyl)thien-3-yl)-3-oxopropanoate (Preparation 19, 51.7 g) in m-xylene (800 mL) is sparged with nitrogen gas for 15 min. 4-Chlorobenzylamine (20.0 mL) is added. The reaction mixture is heated to 140° C. for 2 h with collection of distillate in a Dean-Stark trap. The mixture is allowed to cool to room temperature and is then partially concentrated by rotary evaporation at 65° C. to provide a slurry. The slurry is suspended in diethyl ether (100 mL), filtered, and the resulting solids are washed with a mixture hexanes/diethyl ether (1/1, 100 mL) to afford 48.96 g of the title compound as an off white solid. Physical characteristics. M.p. 109–112° C.; $^1$H NMR (400 MHz, DMSO-d$_6$) δ 8.82, 8.64, 7.43–7.29, 7.11, 5.83, 4.38, 4.29, 3.85, 3.64, 3.62, 3.57, 2.41; $^{13}$C NMR (100 MHz, DMSO-d$_6$) δ 188.8, 172.0, 166.3, 162.8, 140.9, 140.7, 138.6, 138.3, 135.5, 134.0, 131.9, 131.8, 131.7, 129.7, 129.4, 128.7, 128.6, 127.0, 126.6, 125.1, 92.4, 66.5, 56.9, 56.8, 53.2, 49.8, 41.9, 41.6. Anal. Found C, 53.42; H. 4.66; N, 6.50; Cl, 16.53; S, 7.46.

Preparation 21.

N-(4-Chlorobenzyl)-2-((2-chloro-5-(morpholin-4-ylmethyl)thien-3-yl)carbonyl)-3-((2-morpholin-4-ylethyl)amino)acrylamide.

A mixture of N-(4-chlorobenzyl)-3-(2-chloro-5-(morpholin-4-ylmethyl)thien-3-yl)-3-oxopropanamide (Preparation 20, 20.0 g), triethylorthoformate (15.4 mL), and acetic anhydride (15.4 mL) is heated to 150° C. with removal of the distillate with a Dean-Stark trap. After 3 h, the volatiles are removed at 40 Torr (50° C.) and then at 0.2 Torr (100° C.) for 1 h to afford a brown oil. A portion of this residue (10.0 g) is dissolved in ethanol (150 mL) and N-aminoethylmorpholine (4.1 g) is added. The mixture is stirred at room temperature for 24 h and then is concentrated in vacuo. The crude product is purified by column chromatography (CH$_2$Cl$_2$/methanol, 97/3) to afford 4.28 g of the title compound as a brown oil. Physical characteristics. $^1$H NMR (300 MHz, DMSO-d$_6$) δ 10.51, 9.89, 7.62, 7.58, 7.37, 6.92, 4.44, 3.62, 3.58, 3.47, 3.40, 2.42, 2.32.

Preparation 22.

N-(4-Chlorobenzyl)-7-(2-morpholin-5-ylethyl)-2-(morpholin-4-ylmethyl)-4-oxo-4,7-dihydrothieno[2,3-b]pyridine-5-carboxamide.

A mixture of N-(4-chlorobenzyl)-2-((2-chloro-5-(morpholin-4-ylmethyl)thien-3-yl)carbonyl)-3-((2-morpholin-4-ylethyl)amino)acrylamide (Preparation 6, 4.3 g) and K$_2$CO$_3$ (1.6 g) in DMF (75 mL) is stirred at 100° C. for 5 h. The mixture is allowed to cool to room temperature and is concentrated in vacuo. The crude product is triturated with EtOAc and filtered to afford 1.4 g of the title compound as a yellow solid Physical characteristics. $^1$H NMR (300 MHz, DMSO-d$_6$) δ 10.57, 8.71, 7.42–7.32, 4.55, 4.37, 3.74, 3.59, 3.50, 2.73, 2.44; MS (ESI+) m/z 531 (M+H)$^+$.

Preparation 23.

N-(4-Chlorobenzyl)-2-chloromethyl)-7-(2-morpholin-4-ylethyl)-4-oxo-4,7-dihydrothieno[2,3-b]pyridine-5-carboxamide.

N-4-Chlorobenzyl)-7-(2-morpholin-4-ylethyl)-2-(morpholin-4-ylmethyl)-4-oxo-4,7-dihydrothieno[2,3-b]pyridine-5-carboxamide (Preparation 22, 1.3 g) is dissolved in chloroform (300 mL). Ethylchloroformate (0.58 mL) is added, and the mixture is stirred at room temperature for 18 h. Additional ethylchloroformate (0.58 mL) is added and stirring continued for 2 days. The mire is concentrated in vacuo. The residue is triturated with ethyl acetate and filtered. The crude product is recrystallized from acetonitrile to afford 1.4 g of the title compound as a yellow solid. Physical characteristics. ¹H NMR (300 MHz, DMSO-$d_6$) δ 10.46, 8.75, 7.55, 7.42–7.32, 5.15, Example 22
N-(4-Chlorobenzyl)-2-(((2R*)-2-((S*)-hydroxy(phenyl)methyl)pyrrolidin-1-yl)-methyl)-7-(2-morpholin-4-ylethyl)-4-oxo-4,7-dihydrothieno[2,3-b]pyridine-5-carboxamide.

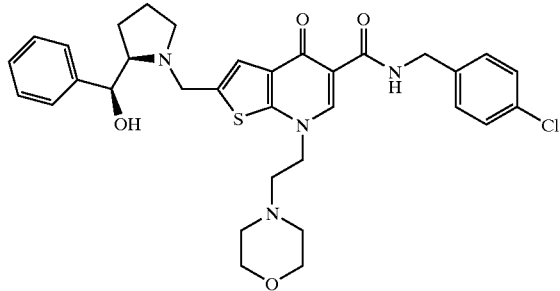

Analogous to the procedures described in Example 2, N-(4-chlorobenzyl)-2-(chloromethyl)-7-(2-morpholin-4-ylethyl)-4-oxo-4,7-dihydrothieno[2,3-b]pyridine-5-carboxamide (Preparation 23) is treated with 2-(hydroxy(phenyl)methyl)pyrrolidine (Preparation 2) to afford the title compound.

Example 23
N-(4-Chlorobenzyl)-2-(((3R)-3-((S)-hydroxy(phenyl)methyl)morpholin-4-yl)-methyl)-7-(2-morpholin-4-ylethyl)-4-oxo-4,7-dihydrothieno[2,3-b]pyridine-5-carboxamide.

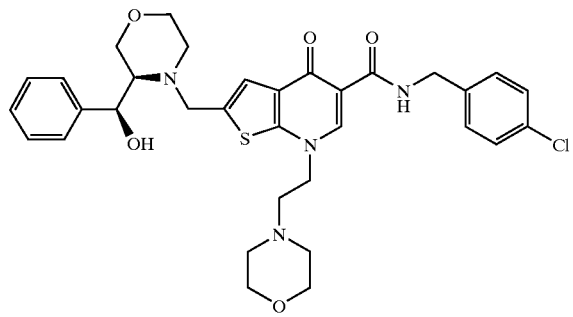

Analogous to the procedures described in Example 15, N-(4-chlorobenzyl)-2-(chloromethyl)-7-(2-morpholin-4-ylethyl)-4-oxo-4,7-dihydrothieno[2,3-b]pyridine-5-carboxamide (Preparation 23) is treated with (S)-(3R)-morpholin-3-yl(phenyl)methanol hydrochloride (Preparation 9) to afford the title compound.

Preparation 24.
Diethyl 2-(((3-(Ethoxycarbonyl)-4-methylthien-2-yl)amino)methylene)malonate.

A mixture of ethyl 2-amino-4-methylthiophene-3-carboxylate (5.23 g) and diethyl ethoxymethylenemalonate (5.71 mL) is heated to 135° C. for 3 h with a stream of nitrogen passing through the flask. The mixture is allowed to cool to room temperature. The resulting solid is recrystallized (EtOH, 250 mL) to afford 9.23 g of the title compound as yellow needles. Physical characteristics. M.p. 126–128° C.; ¹H NMR (400 MHz, DMSO-$d_6$) δ12.36, 8.08, 6.77, 4.34, 4.24, 4.15, 2.31, 1.34, 1.27, 1.25; MS (ESI+) m/z 356 (M+H)⁺. Anal. Found: C, 54.12; H, 5.95; N, 3.99.; S, 8.99.

Preparation 25.
2-((3-Ethoxy-2-ethoxycarbonyl)-3-oxoprop-1-enyl)amino)-4-methylthiophene-3-carboxylic acid.

Potassium hydroxide (1.61 g) is dissolved in ethanol (10 mL) and heated to 70° C. A solution of diethyl 2-(((3-ethoxycarbonyl)-4-methylthien-2-yl)amino)-methylene)malonate (Preparation 24, 1.78 g) in THF (25 mL) is added. The resulting suspension is heated for an additional 2 h and is then allowed to cool to room temperature. The mixture is poured onto ice (250 mL) and the solution is made acidic with concentrated hydrochloric acid The suspension is filtered, washed with 1 N hydrochloric acid, and dried (40 Torr, 75° C., 6 h) to afford 1.13 g of the title compound as a yellow solid. Physical characteristics. M.p. 190–192° C. (dec); ¹H NMR (400 MD, DMSO-$d_6$) δ 13.38, 12.33, 8.08, 6.73, 4.23, 4.15, 2.30, 1.27, 1.24; MS (ESI−) m/z 326 (M−H)⁻.

Preparation 26.
Ethyl 4-Hydroxy-3-methylthieno[2,3-b]pyridine-5-carboxylate.

In a flask equipped with a Dean-Stark trap, a mixture of 2-((3-ethoxy-2-(ethoxycarbonyl)-3-oxoprop-1-enyl)amino)-4-methylthiophene-3-carboxylic acid (Preparation 25, 4.58 g) and phenyl ether (50 mL) is degassed by freeze-pump-thaw method and then heated to reflux. After approximately 30 min, the reaction mixture is allowed to cool to room temperature. The crude mixture is purified by column chromatography ($CH_2Cl_2$; $CH_2Cl_2$/methanol, 100/1) to afford 1.95 g of the title compound as a yellow solid. Physical characteristics. M.p. 189–192° C.; ¹HNMR (400 MHz, $CF_3CO_2D$) δ 11.65, 9.10, 7.31, 4.66, 2.76, 1.53; MS (ESI−) m/z 236 (M—H). Anal. Found: C, 55.66; H, 4.67; N, 5.85; S, 13.40.

Preparation 27.
Ethyl 4-Hydroxy-3-methyl-2-(morpholin-4-ylmethyl)thieno[2,3-b]pyridine-5-carboxylate.

A suspension of ethyl 4-hydroxy-3-methylthieno[2,3-b]pyridine-5-carboxylate (Preparation 26, 0.92 g) and 4-methylenemorpholin-4-ium chloride (1.57 g) in acetonitrile (40 mL) is heated to 60° C. for 4 h. The resulting suspension is allowed to cool to room temperature, poured into water, and adjusted to neutral pH with saturated aq. sodium bicarbonate. The solution is extracted with $CH_2Cl_2$ (3×100 mL). The combined organic layers are washed with brine (25 mL), dried ($Na_2SO_4$), and concentrated to afford 1.26 g of the title compound as a yellow solid. Physical characteristics. M.p. 182–185° C.; ¹H NMR (400 MHz, DMSO-$d_6$) δ 8.64, 4.37, 3.70, 3.38, 2.51, 2.47, 1.35; MS (ESI−) m/z 335 (M-H). Anal. Found: C, 56.93; H, 6.10; N, 8.26; S, 9.34.

Preparation 28.
Ethyl 3,7-Dimethyl-2-(morpholin-4-ylmethyl)-4-oxo-4,7-dihydrothieno[2,3-b]-pyridine-5-caboxylate.

Ethyl 4-hydroxy-3-methyl-2-(morpholin-4-ylmethyl)thieno[2,3-b]pyridine-5-carboxylate (Preparation 27, 1.47 g) and potassium carbonate (1.21 g) are suspended be in DMF (25 mL). The mixture is warmed until the ester dissolves and iodomethane (0.30 mL) is added. The reaction mixture is allowed to stir at room temperature for 20 h. The mixture is then poured into water (100 mL) and extracted with EtOAc (3×100 mL). The combined organic layers are washed with brine (2×25 mL), dried ($Na_2SO_4$), and partially concentrated. Hexanes are added and the resulting solid is filtered to afford 0.70 g of the title compound as a light yellow solids Physical characteristics. M.p. 172–173° C.; ¹H NMR (400 MHz, DMSO-$d_6$) δ 8.41, 4.19, 3.81, 3.65, 3.59, 2.48, 2.46, 1.27; MS (ESI+) m/z 351 (M+H)⁺. Anal. Found: C, 58.04; H, 6.54; N, 7.77; S, 8.97.

Preparation 29.
N-(4-Chlorobenzy)-3,7-dimethyl-2-(morpholin-4-ylmethyl)-4-oxo-4,7-dihydro-thieno[2,3-b]pyridine-5-carboxamide.

A mixture of ethyl 3,7-dimethyl-2-(morpholin-4-ylmethyl)-4-oxo-4,7-dihydrothieno[2,3-b]pyridine-5-carboxylate (Preparation 28, 700 mg) and 4-chlorobenzylamine (1.25 mL) is heated to 190° C. under a nitrogen atmosphere for 1 h. The reaction mixture is allowed to cool briefly and methanol (10 mL) is added. After cooling to room temperature, the product is filtered and washed with methanol and diethyl ether to afford 634 mg of the title compound as a white solid. Physical characteristics. M.p. 222–224° C.; $^1$H NMR (400 MHz, DMSO-$d_6$) δ 10.67, 8.66, 7.41–7.33, 4.52, 3.92, 3.67, 3.59, 2.51, 2.47; MS (ESI+) m/z 446 (M+H)$^+$. Anal. Found: C, 59.11; H, 5.47; N, 9.32; Cl, 7.96; S, 7.17.

Preparation 30.
N-4-Chlorobenzyl-2-(chloromethyl)-3,7-dimethyl-4-oxo-4,7-dihydrothieno[2,3-b]pyridine-5-carboxamide.

N-(4-Chlorobenzyl)-3,7-dimethyl-2-(morpholin-4-ylmethyl)-4-oxo-4,7-dihydrothieno[2,3-b]pyridine-5-carboxamide (Preparation 29, 500 mg) is dissolved in chloroform (10 mL) and ethyl chloroformate (268 μL) is added. The mixture is allowed to stir at room temperature for 24 h. The resulting suspension is diluted with diethyl ether (30 mL), filtered, and washed with diethyl ether to afford 415 mg of the title compound as a white solid. Physical characteristics. M.p. 234–238° C. (dec); $^1$H NMR (400 MHz, DMSO-$d_6$) δ 10.55, 8.71, 7.41–7.39, 5.12, 4.53, 3.93, 2.58; MS (CI) m/z 395 (M+H)$^+$. Anal. Found: C, 54.36; H, 4.11; N, 6.99; Cl, 18.15; S, 7.94.

Example 24
N-(4-Chlorobenzyl)-2-(((2R*)-2-((S*)-hydroxy(phenyl)methyl)pyrrolidin-1-yl)-methyl)-3,7-dimethyl-4-oxo-4,7-dihydrothieno[2,3-b]pyridine-5-carboxamide.

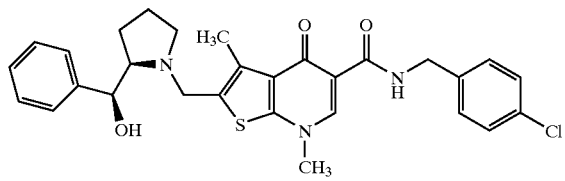

Analogous to the procedures described in Example 2, N-(4-chlorobenzyl)-2-(chloromethyl)-3,7-dimethyl-4-oxo-4,7-dihydrothieno[2,3-b]pyridine-5-carboxamide (Preparation 30) is treated with 2-(hydroxy(phenyl)methyl)pyrrolidine (Preparations 2) to afford the title compound.

Example 25
N-(4-Chlorobenzyl)-2-(((3R)-3-((S)-hydroxy(phenyl)methyl)morpholin-4-yl)-methyl)-3,7-dimethyl 4-xo-4,7-dihydrothieno[2,3-b]pyridine-5-carboxamide.

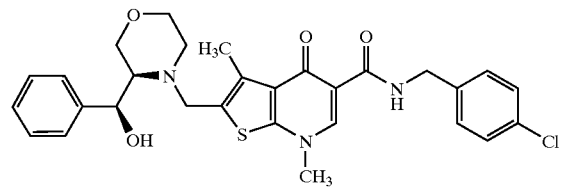

Analogous to the procedures described in Example 15, N-(4-chlorobenzyl)-2-(chloromethyl)-3,7-dimethyl-oxo-4,7-dihydrothieno[2,3-b]pyridine-5-carboxamide (Preparation 30) is treated with (S)-(3R)-morpholin-3-yl(phenyl)methanol hydrochloride (Preparation 9) to afford the title compound.

We claim:
1. A compound of a compound of formula I:

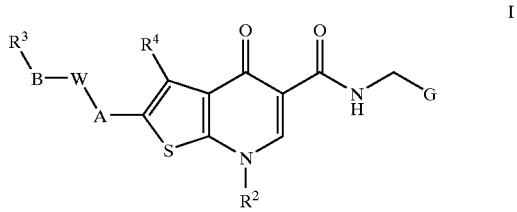

its enantiomeric, diastereomeric, or tautomeric isomer thereof, or a pharmaceutically acceptable salt thereof wherein, G is phenyl substituted with from one (1) to five (5) $R^1$ substituents;

each $R^1$ is independently
(a) Cl,
(b) Br,
(c) F,
(d) CN,
(e) $C_{1-7}$alkyl, or
(f) $NO_2$;

$R^2$ is
(a) H,
(b) $R^5$,
(c) $NR^7R^8$,
(d) $SO_2R^{10}$, or
(e) $OR^6$;

A is $C_{1-7}$alkyl;

W is a five- (5) or six- (6) membered heterocyclic ring having one (1), two (2) or three (3) heteroatoms selected from the group consisting of O, $S(O)_k$, and N wherein W is optionally substituted with one or more OH, oxo (=O), or $C_{1-7}$-alkyl;

B is
(a) $C_{1-7}$alkyl optionally substituted by OH or $NR^7R^8$,
(b) O, or
(c) $NR^{11}$, $R^3$ is
(a) phenyl, optionally fused to a benzene or pyridine ring, and optionally substituted by $R^{12}$, wherein optionally any two adjacent $R^{12}$ substituents taken together constitute a group of the formula —O(CH$_2$)O—, —(NH)C(=O)(CH$_2$)$_j$O—, or (CH$_2$)$_i$—, or
(b) a five- (5) or six- (6) membered heteroaryl bonded via a carbon atom having one (1), two (2), or three (3) heteroatoms selected from the group consisting of O, S, and N—Z, wherein $R^3$ is optionally fused to a benzene or pyridine ring, and optionally substituted with one or more $R^{12}$, wherein Z is absence, H, or $C_{1-4}$alkyl;

$R^4$ is
(a) H,
(b) halo, or
(c) $C_{1-4}$alkyl optionally substituted by halo;

$R^5$ is
(a) $(CH_2)_mOCH_2CH_2OR^{11}$,
(b) het, wherein said het is bound via a carbon atom,
(c) aryl, (d) $C_{1-7}$alkyl which may be partially unsaturated and is optionally substituted by one or more $R^6$ substituents, or
(e) $C_{3-8}$cycloalkyl which may be partially unsaturated and optionally substituted by one or more $R^6$ or $C_{1-7}$alkyl optionally substituted by $R^6$;

$R^6$ is
(a) $OR^9$,
(b) $SR^9$,
(c) $NR^7R^8$,
(d) halo,
(e) $CONR^7R^8$,
(f) $CO_2R^9$,
(g) het,
(h) phenyl, optionally substituted by $R^{12}$,
(i) CN,
(j) oxo,
(k) $SO_2NR^9R^{11}$,
(l) $SO_mR^{10}$, or
(m) $P(=O)(OR^{11})(R^{11})$;

$R^7$ and $R^8$ are independently
(a) H,
(b) aryl,
(c) $C_{1-7}$ alkyl which may be partially unsaturated and is optionally substituted by one or more $NR^{11}R^{11}$, $OR^{11}$, $SR^{11}$, $SO_mR^{10}$, $CONR^{11}R^{11}$, $CO_2R^{11}$, het, aryl, cyano, or halo,
(d) $C_{3-8}$cycloalkyl,
(e) $(C=O)R^{10}$, or
(f) $R^7$ and $R^8$ together with the nitrogen to which they are attached form a het;

$R^9$ is
(a) H,
(b) aryl,
(c) het, wherein the het is bound through a carbon atom,
(d) $C_{1-7}$alkyl which is optionally partially unsaturated and is optionally substituted by one or more aryl, het, $OR^{11}$, $SR^{11}$, $NR^{11}R^{11}$, halo, or $C_{3-8}$cycloalkyl substituents and which $C_{3-8}$cycloalkyl is optionally substituted by $OR^{11}$, or
(e) $C_{3-8}$cycloalkyl which is optionally partially unsaturated and is optionally substituted by one or more halo, $OR^{11}$, $SR^{11}$, or $NR^{11}R^{11}$ substituents;

$R^{10}$ is
(a) aryl,
(b) het,
(c) $C_{1-7}$alkyl which is optionally partially unsaturated and is optionally substituted by one or more aryl, het, $OR^{11}$, $SR^{11}$, $NR^{11}R^{11}$, halo, or $C_{3-8}$cycloalkyl substituents and which $C_{3-8}$cycloalkyl is optionally substituted by $OR^{11}$, or
(d) $C_{3-8}$ cycloalkyl which is optionally partially unsaturated and is optionally substituted by one or more halo, $OR^{11}$, $SR^{11}$, or $NR^{11}R^{11}$ substituents;

$R^{11}$ is
(a) H, or
(b) $C_{1-7}$ alkyl;

$R^{12}$ is
(a) halo,
(b) $OR^{14}$,
(c) $SR^{11}$,
(d) $NR^7R^8$,
(e) phenyl, optionally substituted by halo, $C_{1-7}$alkyl, or $C_{1-7}$alkoxy,
(f) $C_{1-7}$alkyl which is optionally partially unsaturated and optionally substituted by $R^{13}$,
(g) cyano,
(h) nitro,
(i) $CONR^7R^8$,
(j) $SO_2NR^7R^8$,
(k) $CO_2R^{11}$, or
(l) $NHC(=O)R^{11}$;

$R^{13}$ is
(a) phenyl, optionally substituted by halo, $C_{1-7}$alkyl, or $C_{1-7}$alkoxy,
(b) $OR^{11}$,
(c) $O(CH_2CH_2O)_nR^{11}$,
(d) $NR^7R^8$, or
(e) halo;

$R^{14}$ is
(a) H
(b) alkyl optionally substituted by halo,
(c) phenyl, optionally substituted by halo, $C_{1-7}$alkyl, or $C_{1-7}$alkoxy, or
(d) $-(CH_2CH_2O)_nOR^{11}$;

wherein any aryl is optionally substituted with one or more substituents selected from the group consisting of halo, $OR^{11}$, $NR^{11}R^{11}$, cyano, $CO_2R^{11}$, or $C_{1-7}$alkyl in which said $C_{1-7}$alkyl is optionally substituted by one to three halo, $OR^{11}$, or $NR^{11}R^{11}$;

wherein any het is optionally substituted with one or more substituents selected from the group consisting of halo, $OR^{11}$, $NR^{11}R^{11}$, cyano, $CO_2R^{11}$, oxo (=O), or $C_{1-7}$alkyl in which said $C_{1-7}$alkyl is optionally substituted by one to three halo, $OR^{11}$, or $NR^{11}R^{11}$;

i is 3 or 4;
j is 0 or 1;
k is 0, 1, or 2;
each n is independently 1, 2, 3, 4 or 5; and
each m is independently 1 or 2.

2. A compound of claim 1 wherein $R^1$ is F, Cl, or cyano.
3. A compound of claim 2 wherein $R^1$ is Cl.
4. A compound of claim 2 wherein $R^1$ is F.
5. A compound of claim 1 wherein G is 4-chlorophenyl.
6. A compound of claim 1 wherein G is 4-fluorophenyl.
7. A compound of claim 1 wherein $R^2$ is H.
8. A compound of claim 1 wherein $R^2$ is $R^5$.
9. A compound of claim 1 wherein $R^2$ is $NR^7R^8$.
10. A compound of claim 1 wherein $R^2$ is $SO_2R$ % e.
11. A compound of claim 1 wherein $R^2$ is $OR^9$.
12. A compound of claim 8 wherein $R^2$ is $C_{1-7}$ which may be partially unsaturated and is optionally substituted with one or more $R^6$ substituents.
13. A compound of claim 12 wherein $R^2$ is methyl.
14. A compound of claim 12 wherein $R^2$ is ethyl.
15. A compound of claim 1 wherein A is $C_{1-4}$alkyl.
16. A compound of claim 1 wherein A is methyl.
17. A compound of claim 1 wherein W is a six- (6) membered heterocyclic ring having one (1), two (2), or three (3) heteroatoms selected from the group consisting of O, $S(O)_k$, or N, wherein het is optionally substituted with $C_{1-4}$alkyl.
18. A compound of claim 1 wherein W is a five- (5) membered heterocyclic ring having one (1), two (2), or three (3) heteroatoms selected from the group consisting of O, $S(O)_k$, or N, wherein het is optionally substituted with $C_{1-4}$alkyl.
19. A compound of claim 17 wherein W is morpholine.
20. A compound of claim 18 wherein W is pyrrolidine.
21. A compound of claim 1 wherein B is $C_{1-4}$alkyl.
22. A compound of claim 1 wherein B is methyl.
23. A compound of claim 1 wherein B is methyl substituted with a hydroxy.

24. A compound of claim 1 wherein $R^3$ is phenyl.

25. A compound of claim 1 wherein $R^3$ is naphthyl.

26. A compound of claim 1 wherein $R^3$ is phenyl, fused to a pyridine ring.

27. A compound of claim 1 wherein $R^3$ is a five- (5) membered heteroaryl bonded via a carbon atom having one (1) or two (2) heteroatoms selected from the group consisting of O, S, and N—Z.

28. A compound of claim 1 wherein $R^3$ is a five- (5) membered heteroaryl bonded via a carbon atom having one (1) or two (2) heteroatoms selected from the group consisting of O, S, and N—Z, wherein $R^3$ is fused to a benzene or pyridine ring.

29. A compound of claim 1 wherein $R^3$ is a six- (6) membered heteroaryl bonded via a carbon atom having one (1) or two (2) nitrogen atoms.

30. A compound of claim 1 wherein $R^3$ is a six- (6) membered heteroaryl bonded via a carbon atom having one (1) nitrogen atom.

31. A compound of claim 1 wherein $R^3$ is a six- (6) membered heteroaryl bonded via a carbon atom having one (1) or two (2) nitrogen atoms and is fused to a benzene ring.

32. A compound as in any of claims 24–31 wherein $R^3$ is substituted by $R^{12}$.

33. A compound of claim 27 wherein $R^3$ is 2-furyl, thien-2-yl, 1,3-thiazol-2-yl, 1,3-thiazol-5-yl, or 1H-imidazol-2-yl.

34. A compound of claim 29 wherein $R^3$ is pyrimidin-2-yl, or pyrimidin-5-yl.

35. A compound of claim 29 wherein $R^3$ is pyrazin-2-yl.

36. A compound of claim 30 wherein $R^3$ is pyridin-2-yl, or pyridin-3-yl.

37. A compound of claim 1 wherein $R^3$ is 1,3-benzoxazol-2-yl, or 1,3-benzothiazol-2-yl.

38. A compound of claim 1 which is
  (1) 2-(((3S)-3-benzylmorpholin-4-yl)methyl)-N-(4-chlorobenzyl)-7-methyl-4-oxo-4,7-dilydrothieno[2,3-b]pyridine-5-carboxamide,
  (2) N-(4-chlorobenzyl)-2-(((2R*)-2-((S*)-hydroxy(phenyl)methyl)-pyrrolidin-1-yl)methyl)-7-methyl-4-oxo-4,7-dihydrothieno[2,3-b]pyridine-5-carboxamide
  (3) N-(4-Chlorobenzyl)-2-(((2R*)-2-((R*)-hydroxy(pyridin-2-yl)methyl)-pyrrolidin-1-ylmethyl)-7-methyl-4-oxo-4,7-dihydrothieno[2,3-b]pyridine-5-carboxamide,
  (4) N-(4-Chlorobenzyl)-2-(((2R*)-2-((R*)-2-furyl(hydroxy)methyl)-pyrrolidin-1-yl)methyl)-7-methyl-4-oxo-4,7-dihydrothieno[2,3-b]pyridine-5-carboxamide,
  (5) N-(4-chlorobenzyl)-2-(((2R)-2-((R)-hydroxy(1,3-thiazol-2-yl)methyl)-pyrrolidin-1-yl}methyl)-7-methyl-4-oxo-4,7-dihydrothieno[2,3-b]pyridine-5-carboxamide,
  (6) N-(4-chlorobenzyl)-2-(((2R)-2-((R)-hydroxy(thien-2-yl)methyl)-pyrrolidin-1-yl}methyl)-7-methyl-4-oxo-4,7-dihydrothieno[2,3-b]pyridine-5-carboxamide,
  (7) 2-(((2R)-2-((R)-1,3-benzothiazol-2-yl(hydroxy)methyl)pyrrolidin-1-yl)-methyl)-N-(4-chlorobenzyl)-7-methyl-4-oxo-4,7-dihydrothieno[2,3-b]pyridine-5-carboxamide,
  (8) N-(4-chlorobenzyl)-2-(((2R)-2-((R)-hydroxy(1,3-thiazol-5-yl)methyl)-pyrrolidin-1-yl)methyl)-7-methyl-4-oxo-4,7-dihydrothieno[2,3-b]pyridine-5-carboxamide,
  (9) N-(4-chlorobenzyl)-2-(((2R)-2-((R)-hydroxy(pyridin-2-yl)methyl)-pyrrolidin-1-yl)methyl)-7-methyl-4-oxo-4,7-dihydrothieno[2,3-b]pyridine-5-carboxamide,
  (10) N-(4-chlorobenzyl)-2-(((2R)-2-((S)-hydroxy(pyridin-3-yl)methyl)-pyrrolidin-1-yl)methyl)-7-methyl-4-oxo-4,7-dihydrothieno[2,3-b]pyridine-5-carboxamide,
  (11) N-(4-chlorobenzyl)-2-(((2R)-2-((S)-hydroxy(pyrimidin-5-yl)methyl)-pyrrolidin-1-yl)methyl)-7-methyl-4-oxo-4,7-dihydrothieno[2,3-b]pyridine-5-carboxamide,
  (12) N-(4-chlorobenzyl)-2-(((2R)-2-((R)-hydroxy(1H-imidazol-2-yl)-methyl)pyrrolidin-1-yl)methyl)-7-methyl-4-oxo-4,7-dihydrothieno[2,3-b]pyridine-5-carboxamide,
  (13) 2-(((2R)-2-((R)-1,3-benzoxazol-2-yl(hydroxy)methyl)pyrrolidin-1-yl)-methyl)-N-4-chlorobenzyl)-7-methyl-4-oxo-4,7-dihydrothieno[2,3-b]pyridine-5-carboxamide,
  (14) N-(4-chlorobenzyl)-2-(((3R)-3-((R)-hydroxy(phenyl)methyl)morpholin-4-yl)methyl)-7-methyl-4-oxo-4,7-dihydrothieno[2,3-b]pyridine-5-carboxamide,
  (15) N-(4-chlorobenzyl)-2-(((3R)-3-((S)-hydroxy(phenyl)methyl)morpholin-4-yl)methyl)-7-methyl-4-oxo-4,7-dihydrothieno[2,3-b]pyridine-5-carboxamide,
  (16) N-(4-chlorobenzyl)-7-ethyl-2-(((2R*)-2-((S*)-hydroxy(phenyl)methyl)-pyrrolidin-1-yl)methyl)-4-oxo-4,7-dihydrothieno[2,3-b]pyridine-5-carboxamide,
  (17) N-(4-chlorobenzyl)-7ethyl-2-(((3R)-3-((S)-hydroxy(phenyl)methyl)-morpholin-4-yl)methyl)-4-oxo-4,7-dihydrothieno[2,3-b]pyridine-5-carboxamide,
  (18) N-(4-chlorobenzyl)-2-(((2R*)-2-((S*)-hydroxy(phenyl)methyl)-pyrrolidin-1-yl)methyl)-4-oxo-7-propyl-4,7-dihydrothieno[2,3-b]pyridine-5-carboxamide,
  (19) N-(4-chlorobenzyl)-2-(((3R)-3-((S)-hydroxy(phenyl)methyl)morpholin-4-yl)methyl)-4-oxo-7-propyl-4,7-dihydrothieno[2,3-b]pyridine-5-carboxamide,
  (20) N-(4-chlorobenzyl)-2-(((2R*)-2-((S*)-hydroxy(phenyl)methyl)-pyrrolidin-1-yl)methyl)-7-(2-methoxyethyl)-4-oxo-4,7-dihydrothieno[2,3-b]-pyridine-5-carboxamide,
  (21) N-(4-chlorobenzyl)-2-(((3R)-3-((S)-hydroxy(phenyl)methyl)morpholin-4-yl)methyl)-7-(2-methoxyethyl)-4-oxo-4,7-dihydrothieno[2,3-b]pyridine-5-carboxamide,
  (22) N-(4-chlorobenzyl)-2-(((2R*)-2-((S*)-hydroxy(phenyl)methyl)-pyrrolidin-1-yl)methyl)-7-(2,3-morpholin-4-ylethyl)-4-oxo-4,7-dihydrothieno[2,3-b]pyridine-5-carboxamide,
  (23) N-(4-chlorobenzyl)-2-((3R)-3-((S)-hydroxy(phenyl)methyl)morpholin-4-yl)methyl)-7-(2-morpholin-4-ylethyl)-4-oxo-4,7-dihydrothieno[2,3-b]-pyridine-5-carboxamide,
  (24) N-(4-chlorobenzyl)-2-((2R*)-2-((S*)-hydroxy(phenyl)methyl)-pyrrolidin-1-yl)methyl)-3,7-dimethyl-4-oxo-4,7-dihydrothieno[2,3-b]pyridine-5-carboxamide,
  (25) N-(4-chlorobenzyl)-2-(((3R)-3-((S)-hydroxy(phenyl)methyl)morpholin-4-yl)methyl)-3,7-dimethyl-4-oxo-4,7-dihydrothieno[2,3-b]pyridine-5-carboxamide, or a pharmaceutically acceptable salt thereof.

39. A compound of claim 1 which is
  (1) 2-((3S)-3-benzylmorpholin-4-yl)methyl)-N-(4-chlorobenzyl)-7-methyl-4-oxo-4,7-dihydrothieno[2,3-b]pyridine-5-carboxamide, (2) N-(4-chlorobenzyl)-2-(((2R*)-2-((S*)-hydroxy(phenyl)methyl)-pyrrolidin-1-yl)methyl)-7-methyl-4-oxo-4,7-dihydrothieno[2,3-b]pyridine-5-carboxamide (3) N-(4-Chlorobenzyl)-2-(((2R*)-2-((R*)-hydroxy(pyridin-2-ylmethyl)-pyrrolidin-1-ylmethyl)-7-methyl-4-oxo-4,7-dihydrothieno[2,3-b]pyridine-5-carboxamide, (4) N-(4-chlorobenzyl)-2-(((3R)-3-((R)-hydroxy(phenyl)methyl)morpholin-4-yl)methyl)-7-methyl-4-oxo-4,7-dihydrothieno[2,3-b]pyridine-5-carboxamide, (5) N-(4-chlorobenzyl)-2-(((3R)-3-((S)-hydroxy(phenyl)methyl)morpholin-4-ylmethyl)-7-methyl-4-oxo-4,7-dihydrothieno[2,3-b]pyridine-5-carboxamide, or a pharmaceutically acceptable salt thereof.

40. A compound of claim 1 which is N-(4-chlorobenzyl)-2-(((2R*)-2-((S*)-hydroxy(phenyl)methyl)pyrrolidin-1-yl)methyl)-7-methyl-4-oxo-4,7-dihydrothieno[2,3-b]pyridine-5-carboxamide, or a pharmaceutically acceptable salt thereof.

41. A compound of claim 1 which is N-(4-chlorobenzyl)-2-(((3R)-3-((S)-hydroxy-(phenyl)methyl)morpholin-4-yl)methyl)-7-methyl-4-oxo-4,7-dihydrothieno[2,3-b]pyridine-5-carboxamide, or a pharmaceutically acceptable salt thereof.

42. A compound of claim 1, or a pharmaceutically acceptable salt thereof, for use in the manufacture of medicines for the treatment or prevention of a herpesviral infection in a mammal.

43. A pharmaceutical composition comprising a compound of claim 1 and a pharmaceutically acceptable carrier.

44. A method of treating infections by herpesviruses which comprises administering to a mammal in need thereof a compound of claim 1.

45. The method of claim 44 wherein said herpesviruses is herpes simplex virus types 1, herpes simplex virus types 2, varicella zoster virus, human cytomegalovirus, Epstein-Barr virus, human herpes virus 6, human herpes virus 7 or human herpes virus 8.

46. The method of claim 45 wherein said herpesvirus is human cytomegalovirus.

47. The method of claim 45 wherein said herpesviruses is varicella zoster virus or Epstein-Barr virus.

48. The method of claim 45 wherein said herpesviruses is herpes simplex virus types 1 or herpes simplex virus types 2.

49. The method of claim 44 wherein the compound of claim 1 is administered orally, parenterally or topically.

50. The method of claim 44 wherein the compound of claim 1 is in an amount of from about 0.1 to about 300 mg/kg of body weight.

51. The method of claim 44 wherein the compound of claim 1 is in an amount of from about 1 to about 30 mg/kg of body weight.

52. The method of claim 44 wherein said mammal is a human.

53. The method of claim 44 wherein said mammal is an animal.

54. A method of treating atherosclerosis and restenosis comprising administering to a mammal in need thereof a compound of claim 1.

55. A method for inhibiting a herpesviral DNA polymerase, comprising contacting the polymerase with an effective inhibitory amount of a compound of claim 1.

* * * * *